(12) United States Patent
Baru Fassio et al.

(10) Patent No.: US 7,636,602 B2
(45) Date of Patent: Dec. 22, 2009

(54) FULLY IMPLANTABLE NERVE SIGNAL SENSING AND STIMULATION DEVICE AND METHOD FOR TREATING FOOT DROP AND OTHER NEUROLOGICAL DISORDERS

(75) Inventors: Marcelo Daniel Baru Fassio, Surrey (CA); Joaquin Andres Hoffer, Anmore (CA); Enric Calderon, Barcelona (ES); Gary Bernhard Jenne, Aldergrove (CA); Albert Calderon, Barcelona (ES)

(73) Assignee: Neurostream Technologies General Partnership, Saint-Augustin-de-Desmaures, Quebec (CA)

(*) Notice: Subject to any disclaimer, the term of this patent is extended or adjusted under 35 U.S.C. 154(b) by 124 days.

(21) Appl. No.: 10/817,158

(22) Filed: Apr. 2, 2004

(65) Prior Publication Data

US 2005/0010265 A1    Jan. 13, 2005

Related U.S. Application Data

(60) Provisional application No. 60/460,275, filed on Apr. 2, 2003.

(51) Int. Cl.
*A61N 1/00* (2006.01)
(52) U.S. Cl. ...................................... 607/48
(58) Field of Classification Search ............ 607/48, 607/49, 61, 144, 116; 623/11.11
See application file for complete search history.

(56) References Cited

U.S. PATENT DOCUMENTS

| 4,750,499 | A | * | 6/1988 | Hoffer | 607/116 |
|---|---|---|---|---|---|
| 5,038,781 | A | * | 8/1991 | Lynch | 607/61 |
| 6,415,181 | B1 | | 7/2002 | Schu et al. | |
| 6,996,435 | B2 | | 2/2006 | Baru Fassio | |
| 2002/0055779 | A1 | * | 5/2002 | Andrews | 623/11.11 |
| 2002/0188331 | A1 | | 12/2002 | Fang et al. | |
| 2003/0144710 | A1 | * | 7/2003 | Haugland et al. | 607/48 |
| 2004/0164783 | A1 | | 8/2004 | Baru Fassio | |

FOREIGN PATENT DOCUMENTS

| CA | 2097857 | 6/1993 |
|---|---|---|
| WO | WO 01/60445 | 8/2001 |
| WO | WO 02/13695 | 2/2002 |

OTHER PUBLICATIONS

Alvarez; BiCMOS Tecnology and Applications; 1993; pp. 317-318; 2nd Edition; Kulwer Academic Publishers.
Andres et al.; "How to Use Nerve Cuffs to Stimulate . . . "; Neural Prothesis; 2001; pp. 139-175.
Binkley et al.; "A Micropower CMOS, Direct-Coversion . . . "; IEEE Journal of Solid-State Circuits; Mar. 1998; pp. 344-358; vol. 33; issue 3.

(Continued)

*Primary Examiner*—George Manuel
(74) *Attorney, Agent, or Firm*—Timothy Keefer Polsinelli Shughart

(57) ABSTRACT

A fully implantable nerve stimulation system includes an event-triggered, closed-loop control unit that detects physiological events from nerve signals and delivers stimulation pulses to a nerve to produce a desired physiological response. The stimulation system includes a low-noise, low-power nerve signal amplifier, accelerometers that detect position and a battery powered processor that selectively powers components in the system to detect physiological events and deliver stimulation pulses with a minimum of battery power.

81 Claims, 20 Drawing Sheets

OTHER PUBLICATIONS

Donaldson et al.; "An Implantable Telemeter For Long-Term . . . "; Proceedings of the 5th Annual Confernence of the International Functional Electrical Stimulation Society.

Enz et al. ; "An Analytical MOS Transistor Model . . . "; Analog Integrated Circuit Signal Processing; 1995; pp. 83-114; vol. 8.

Gray et al.; "MOS Operational Amplifier Design . . . "; IEEE Journal of Solid-State Circuits; 1982; pp. 969-982; vol. sc-17; issue 6.

Gregorian et al.; "Analog MOS Integrated Circuits for Signal Processing"; 1986; pp. 131-133; John Wiley & Sons.

Haugland et al.; "Slip Information Provided by Nerve Cuff . . . "; IEEE Transanctions on Rehabilitation Engineering; 1994; pp. 29-36; vo. 2; issue 1.

Jindal; "Noise Associated with Distributed Resistance . . . "; IEEE Transactions on Electron Devices; 1984; pp. 1505-1509; vol. 31; issue 10.

Nicollini et al.; "A 3,3-V 800-n rms Noise . . . "; IEEE Journal of Solid-State Circuits; 1998; pp. 915-921; vol. 28; issue 8.

Nikolic et al.; "Instrumentation for ENG and . . . "; IEEE Transactions on Biomedical Engineering; 1994; pp. 703-706; vol. 41; issue 7.

Papathanasiou et al.; "An Implantable CMOS Signal . . . "; IEEE International Symposiun on Circuits and Systems; 2000.

Sackinger et al.; "A General Relationship Between Amplifier Parameters . . . "; IEEE Transactions on Circuits and Systems; 1991; pp. 1173-1181; vol. 38; issue 10.

Sackinger et al.; "A Versatile Building Block . . . "; IEEE Journal of Solid-State Circuits; 1987; pp. 287-294; vol. SC-22; issue 2.

Silveria et al.; "A gm-IsubD Based Methodology . . . "; IEEE Journal of Solid-State Circuits; 1996; pp. 1314-1319; vol. 31; issue 9.

Sinkjaer et al.; "Electroneurographic ENG Signals from . . . "; Proceedings of the 5th Annual Confernence of the International Functional Electrical Stimulation Society.

Strange et al.; "Gait Phase Information Provided . . . "; IEEE Transactions on Biomedical Engineering; 1999; pp. 797-809; vol. 46; issue 7.

Vittoz; "Micropower Techniques, Design of Analog-Digital VLSI Circuits for Telecommunications . . . "; 1993; pp. 53-67.

* cited by examiner

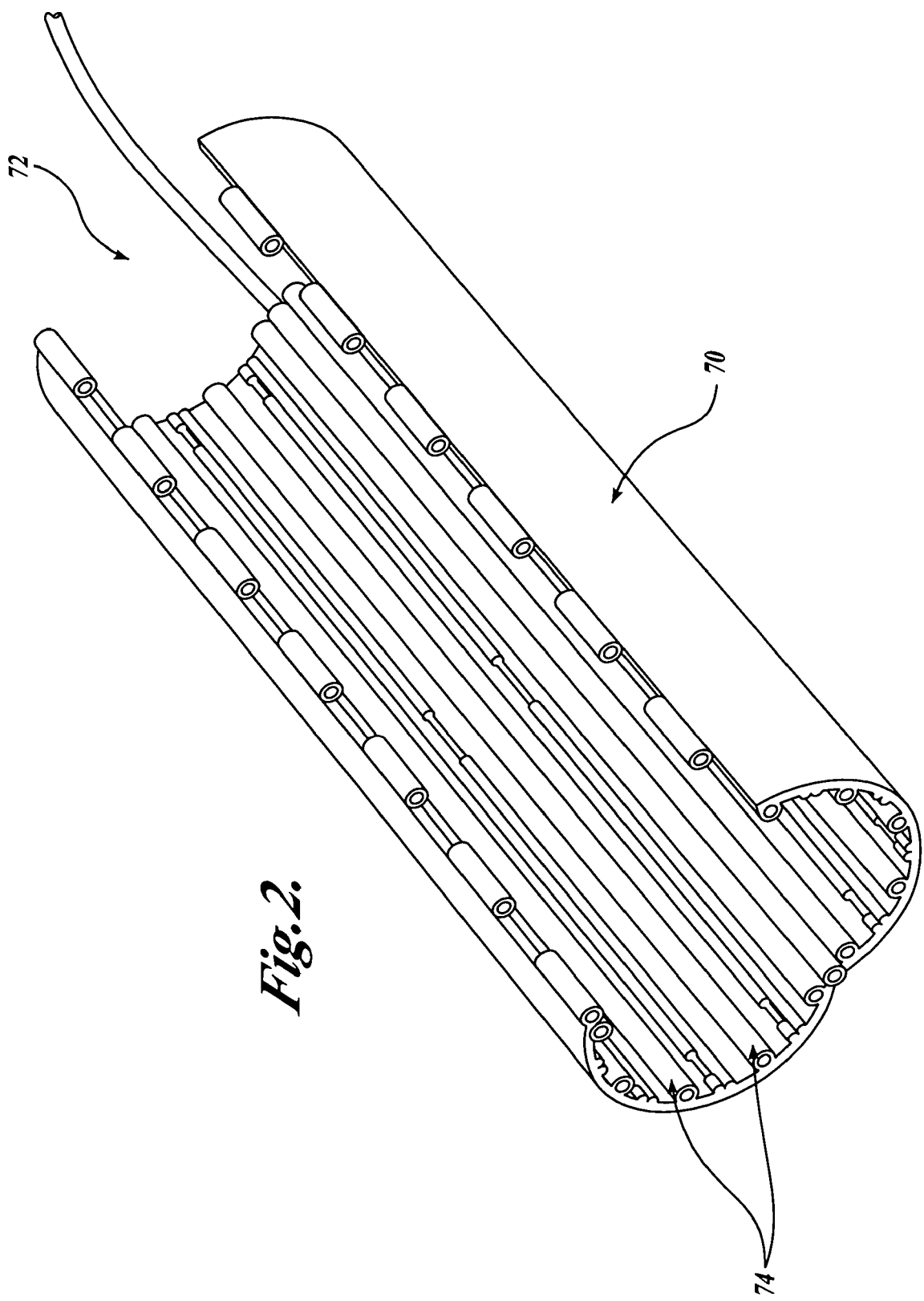

FULLY IMPLANTABLE NERVE SIGNAL SENSING AND STIMULATION DEVICE AND METHOD FOR TREATING FOOT DROP AND OTHER NEUROLOGICAL DISORDERS

CROSS-REFERENCE TO RELATED APPLICATION

The present application claims the benefit of U.S. Provisional Application No. 60/460,275, filed Apr. 2, 2003, which is herein incorporated by reference.

FIELD OF THE INVENTION

The present invention relates to medical devices in general and to nerve stimulation devices in particular.

BACKGROUND OF THE INVENTION

Foot drop is a severely disabling condition that commonly occurs as a consequence of a cerebral vascular accident or central neurological lesion in the cortex, brain stem and/or spinal cord, such as can occur with stroke, multiple sclerosis, brain cancer, traumatic brain injury, incomplete spinal cord injury, or cerebral palsy. The resulting paralysis or paresis in the ankle dorsiflexor muscles prevents a person from lifting the affected foot such that the foot is dragged and the toes stumble during walking. When the cause of the foot drop is a central neurological lesion, the ankle dorsiflexor musculature and the peripheral innervation via the common peroneal nerve are physiologically intact. However, as a consequence of the paralysis or paresis, a complex pathological sequelae develops that includes ankle extensor muscle spasticity, clonus and hyperextension, weakness in hip and knee flexor muscles, marked atrophy in the ankle dorsiflexor muscles due to disuse, compensatory gait and posture abnormalities that include hip circumduction and knee hyperextension, and pain and chronic joint problems frequently result from gait and posture abnormalities.

The foot drop disability commonly results in several impairments in gait, such as asymmetries, poor weight support in the affected leg, slow and laborious walking, impairments in posture and balance, as well as reduced endurance, rapid fatigue and high metabolic cost of walking. The foot drop condition interferes with activities of daily living such as mobility and independence and increase morbidity through increased risk of falls and hip fracture.

Until now, people suffering from foot drop have been treated primarily with ankle-foot orthoses, which are braces that clamp the ankle joint at a set angle, allowing limited or no mobility. This helps the foot drop patient when walking, since the toes no longer stumble. However, the treatment has numerous problems. The sustained pressure applied to the leg and the skin below the knee can cause pain, skin breakdown, and even peroneal nerve palsy. Use of a brace also reinforces the process of progressive atrophy of the disused dorsiflexor muscles and the onset of osteoporosis. The brace must be donned and doffed and may not be cosmetically acceptable, especially by children.

A more advanced approach for treating foot drop involves the application of electrical stimulation (ES), also known as functional electrical stimulation (FES) or functional neuromuscular stimulation (FNS) to the peroneal nerve in order to electrically activate the paralyzed or paretic muscles at appropriate times to lift the foot during walking.

Currently available, the FES systems for treating foot drop have been either totally external to the body or partially implanted with certain components implanted and other components external to the body. The totally external stimulation systems typically consist of stimulation electrodes that are placed on the skin over the area below the knee where the common peroneal nerve courses quite superficially, as well as a battery power source, a sensor (typically either a foot contact electromechanical switch worn in or under the shoe, or an accelerometer-based movement sensor) and the stimulation control circuitry. Problems with totally external stimulation systems have included excessive foot eversion produced with a single channel of stimulation, difficulties with electrode placement, variable results because of electrode movement or changes to skin conductance, pain or discomfort caused by the skin stimulation as well as the requirement for daily donning and doffing. Frequent malfunctions and breakdowns of mechanical switches and external cables are also common. Furthermore, such systems are cosmetically poor.

Historically, the Neuromuscular Assist (NMA) developed in 1968-1977 by McNeal, Perry and Waters at Rancho Los Amigos Hospital, CA was the first partially implanted peroneal nerve stimulation system. It consisted of three parts: an external power source and RF transmitter, an implanted receiver connected to a bipolar electrode wrapped around the peroneal nerve, and a heel switch worn inside the shoe that initiated stimulation during the swing phase. This team implanted 16 patients between November 1971 and January 1974 and did a two-year follow-up study. Correction of foot drop was obtained in 13 of 16 subjects. Failures were due to infection, peroneal palsy, or discontinued use. Stimulation voltages were stable after six weeks and the conduction velocity of the peroneal nerve was normal throughout the duration of the study. Dorsiflexion torque (supramaximal stimulation) remained above immediate postoperative values. However, the NMA device proved not to be practical. One of the original developers of the NMA reported the following limitations with that device:

Intact cognition and considerable patient motivation were required to wear and operate the equipment on a daily basis; and It was difficult to obtain balanced dorsiflexion with a single channel of stimulation.

Dr. Waters concluded in 1977 that broad acceptance of a foot drop correction system will require a totally implanted system and he also anticipated then that multi-channel peroneal stimulation will be necessary in order to obtain more balanced dorsiflexion. In the intervening time, numerous other FES-based foot drop systems have been developed but, prior to the present invention, no totally implanted foot drop correction device has been developed.

In partially implanted systems used to date, the implanted components typically include one or more stimulation electrodes, an implanted receiving antenna, and sometimes some stimulation circuitry. The external components generally include the power source, sensors, and circuitry or a computer to detect the occurrence of gait-related events in the sensed signal, as well as external antenna for communication and power transmission. Some partially implanted FES systems for treating foot drop use radio frequency telemetry communication for on-line control of the stimulation circuits by the external closed-loop control unit and sometimes also for communication between the external sensors and the external control circuitry. Problems with partially implanted FES systems for treating foot drop include: the need to don/doff the external components, crude on-off control, and the requirement that users must wear a shoe when the foot switches are used. Finally, currently available systems have been known to exhibit frequent breakdown of mechanical sensors or external connecting wires and problems with aligning the internal and external antenna for safe communication and operation.

More advanced, partially implanted systems under development are designed to detect a physiological signal that is gait-related and can be sensed by implanted nerve sensing electrodes, such as a nerve cuff electrode placed on a peripheral nerve supplying the foot sole, and such sensed nerve signal may be used as feedback signal to control a stimulation device, as was originally taught by Hoffer (1988). Strange and Hoffer (1999a, 1999b) implemented in the cat forelimb a real time FES state controller that was designed to sense natural sensory nerve signals using nerve cuff electrodes and use the sensed signals as feedback to control the timing of activation with FES of the Palmaris Longus muscle during walking on a treadmill. Thus, the principle of using sensory nerve signals as feedback to control FES of paralyzed or paretic muscles is well understood. However, until now it has been impossible to implement feedback from nerve signals in fully implanted, clinically applicable FES systems, because of the unavailability of suitable implantable circuitry to amplify and process the signals sensed from nerves and to reliably detect the needed gait-related event information from the sensed nerve signals.

However, a limitation in the ability to implement this approach until now has been the unavailability of suitable implantable circuitry to amplify and process the signals sensed from nerves and to reliably detect the gait-related events from the sensed nerve signals.

Given these problems and limitations of existing foot drop systems, there is a need for a low power, totally implantable, event-triggered, closed-loop electrical stimulation system for controlling foot drop or other disorders to restore appropriate movement to an impaired foot, leg or other body part as needed for walking, postural adjustments, or other normal activities for daily living.

SUMMARY OF THE INVENTION

To address the problems discussed above, the present invention is a totally implantable, event-triggered, closed-loop electrical stimulation system for selectively stimulating nerve fibers in order to produce a desired physiological response, such as alleviating foot drop.

The nerve stimulation system includes a battery-powered implantable sensing and electrical stimulation control unit and one or more nerve cuffs having a number of electrodes therein that detect signals from a nerve and deliver stimulation to a nerve. The closed-loop control unit includes a number of signal conditioning circuits that condition the nerve signals sensed by the electrodes. The processed nerve signals are provided to a low-power processor or microcontroller that executes an event detection algorithm to detect the occurrence of a physiological event from the signals. Detection of an event triggers the processor to cause one or more stimulation pulses to be applied to a nerve in order to elicit a desired physiological response. The processor is also programmed to monitor the position of a limb or body segment and shut down circuitry when the user is not standing in order to minimize battery power consumption and thus lengthen the expected life of the battery.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 illustrates an embodiment of a multi-channel nerve cuff for use with the present invention;

DETAILED DESCRIPTION OF THE PREFERRED EMBODIMENT

As indicated above, the present invention is a totally implantable system for selectively sensing gait-related events from sensory nerve signals and for electrically stimulating nerve fibers in order to produce a desired movement or physiological response. Although the disclosed embodiment is directed for alleviating foot drop, it will be appreciated that the invention could be used to alleviate other conditions, such as bladder incontinence, obstructive sleep apnea, phrenic nerve stimulation, control of prosthetic limbs, etc., by programming the device to detect different features from nerve signals sensed from a certain nerve and to stimulate the same or different nerve fibers.

Figure 1A:
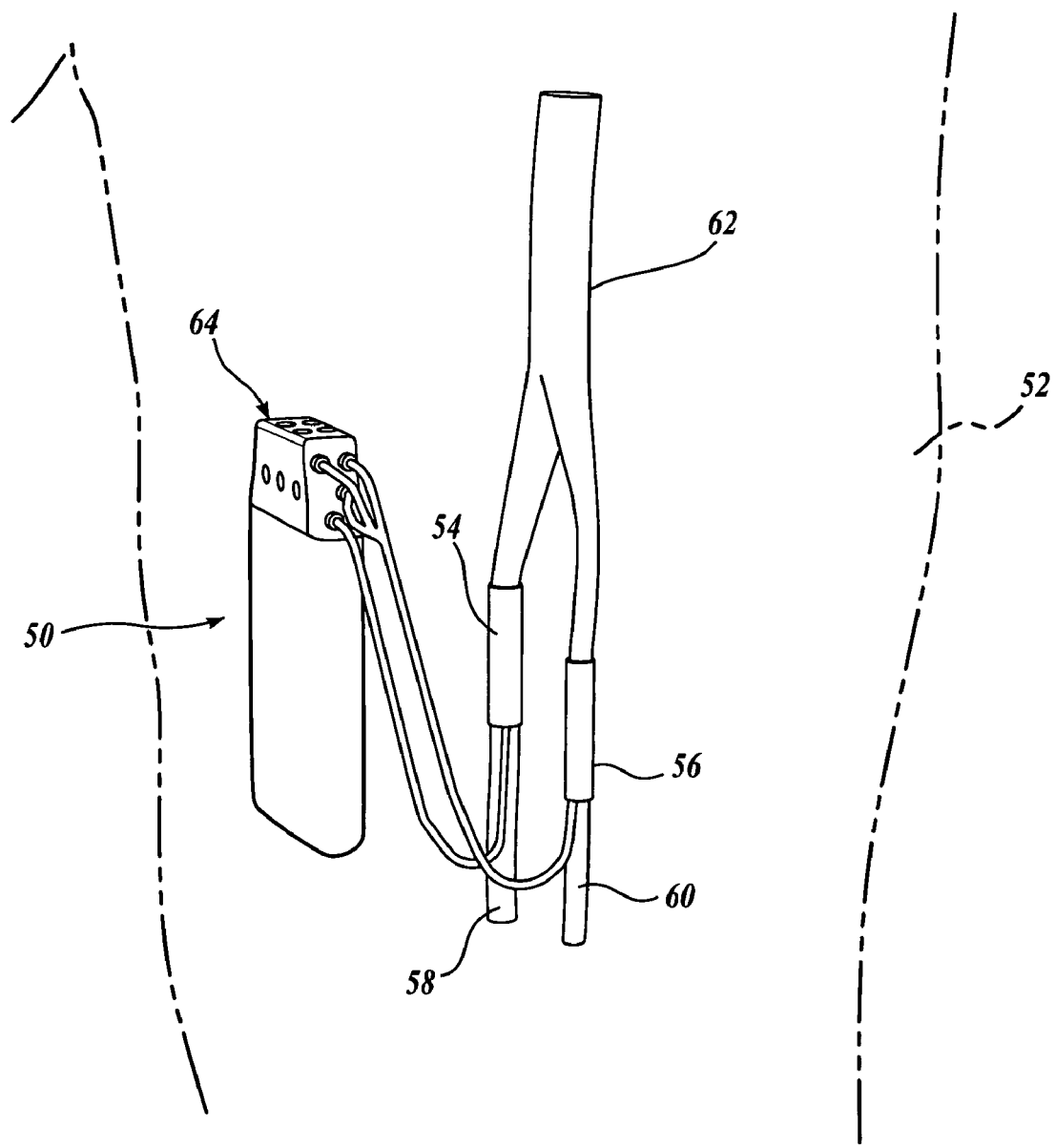
FIG. 1A illustrates the placement of an embodiment of an implantable nerve sensing and electrical stimulation system for treating foot drop having nerve cuffs positioned around the tibial and common peroneal nerves of a patient.

As shown in FIG. 1A, a closed-loop nerve stimulation system of the present invention includes an implanted sensing and electrical stimulation control unit 50 that is surgically positioned entirely within the thigh 52 of a patient. The closed-loop control unit 50 receives sensed sensory nerve signals from electrodes within one or both of a pair of nerve cuffs 54, 56. The sensing nerve cuff 54 is positioned around the tibial nerve 58, and the multi-channel nerve cuff 56 is positioned around the common peroneal nerve 60 that branches from the sciatic nerve 62. The closed-loop control unit 50 is housed within a sealed case, such as titanium or other material of accepted medical use that allows the closed-loop control unit to be located in the body without being harmed by body fluids or producing adverse physiological effects. A header 64 provides a connection between the circuitry included within the closed-loop control unit 50 and the electrodes that are included in the nerve cuffs 54, 56. The header 64 is preferably encased in an epoxy material similar to those commonly used in implantable heart pacemakers.

The closed-loop control unit 50 and nerve cuffs 54, 56 are preferably entirely implanted proximal to the patient's knee so that the leads that connect the closed-loop control unit 50 to the nerve cuffs 54, 56 are as short as practicable and do not cross any joint in the patient. Such a placement minimizes the chance that the leads will fail due to repeated bending of the wires and insulation during movement of the leg, and also maximizes the mechanical stability of the nerve cuffs on the nerves. In the embodiment shown in FIG. 1A, the nerve cuff 54 that is positioned around the tibial nerve 58 is used to detect walking events such as heel contact (HC) and toe lift (TL) that mark the phase transitions of a patient's gait. Upon detection of a toe lift event, the closed-loop control unit 50 delivers one or more stimulating pulses to one or more electrodes within the nerve cuff 56 that is positioned around the common peroneal nerve 60. The stimulating pulses cause the dorsiflexor muscles in the front of the leg to contract and lift the foot and toes in order to alleviate foot drop during the swing phase of gait. Upon detection of the subsequent heel contact event, the control unit 50 stops delivering stimulating pulses to the electrodes within the nerve cuff 56 that is positioned around the common peroneal nerve 60 in order to allow the foot to make full contact with the ground and support the weight of the patient during the stance phase of gait.

In some instances, it is possible to reliably detect both the heel contact (HC) and toe lift (TL) events from the same nerve that is used to stimulate the foot dorsiflexor muscles. In this case, the nerve stimulation system shown in FIG. 1B can be used. In this embodiment, the closed-loop control unit 50 has a single nerve cuff 56 disposed around the common peroneal nerve 60. The electrodes in the nerve cuff 56 are used to detect the heel contact and toe lift events from the sensed sensory nerve signals as well as to supply stimulation pulses to the common peroneal nerve 60 in order to move the foot at the appropriate time of the patient's step.

In other patients, the location of the branch point where the tibial nerve 58 and common peroneal nerve 60 separate from the sciatic nerve 62 occurs very distally within the thigh, making it difficult for a surgeon to place a nerve cuff around a nerve branch below the bifurcation. In such case, the embodiment shown in FIG. 1C can be used. In this embodiment, a closed-loop control unit 50 is coupled to a single, multi-channel nerve cuff 66 that is positioned around the entire sciatic nerve 62. Electrodes within the nerve cuff 66 sense the heel contact (HC) and toe lift (TL) events as well as supply stimulation signals to the appropriate common peroneal nerve fibers coursing within the sciatic nerve 62 in order to move the foot at the desired time in the patient's step.

Figure 1B:
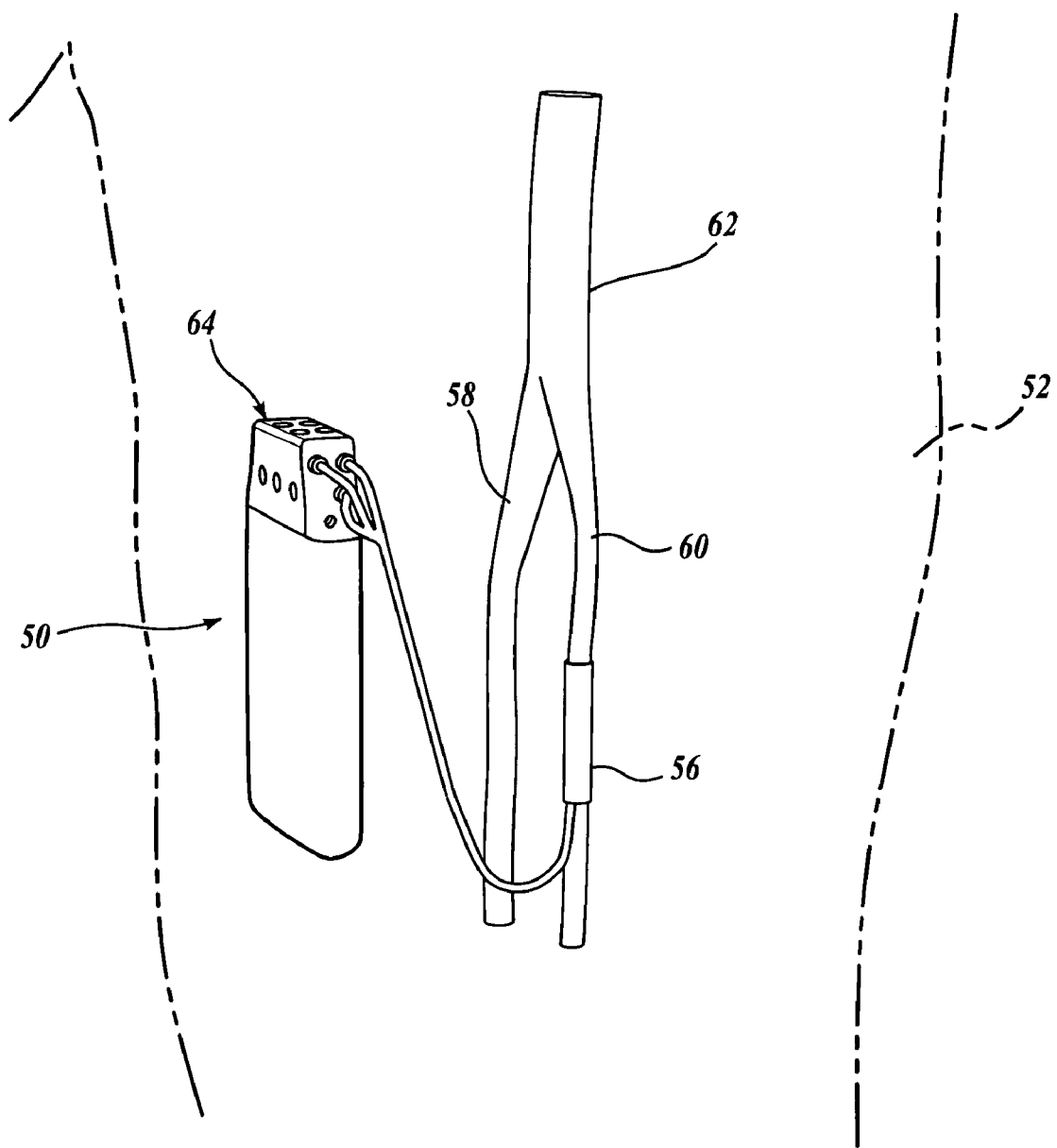
FIG. 1B illustrates another embodiment of an implantable nerve signal sensing and electrical stimulation system for treating foot drop in accordance with the present invention having a single nerve cuff positioned around the common peroneal nerve of a patient.
Figure 1C:
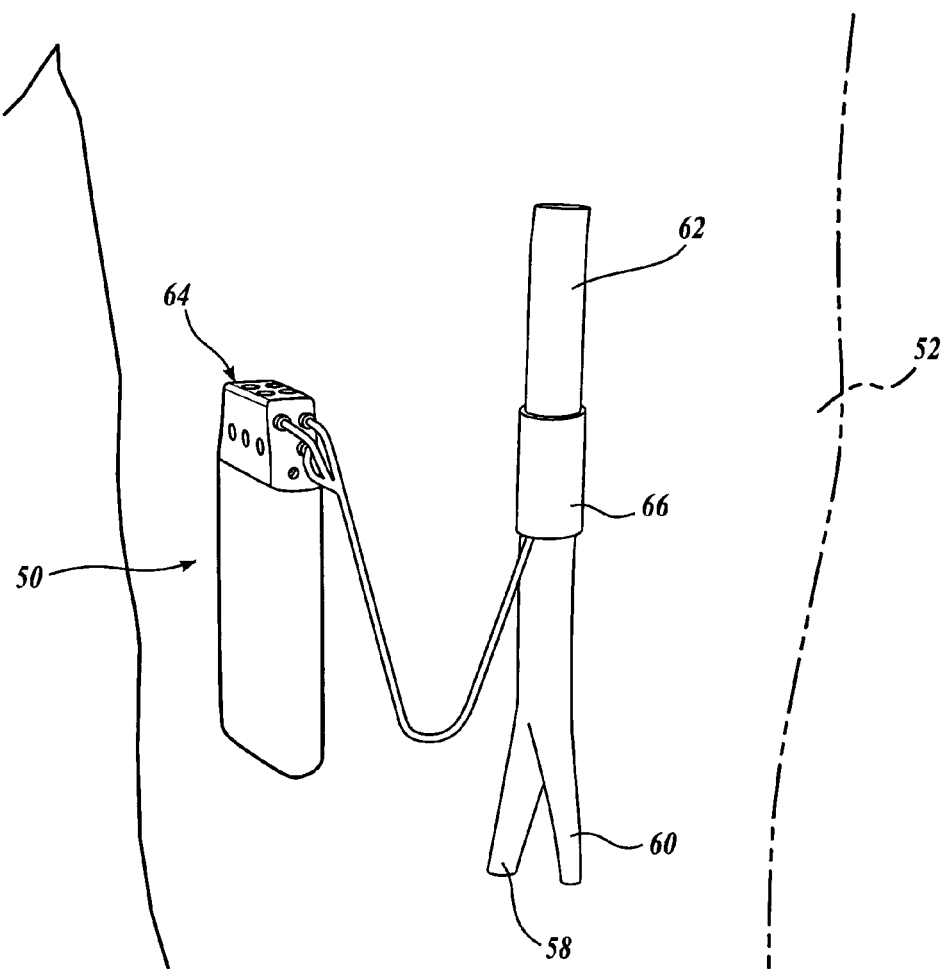
FIG. 1C illustrates another embodiment of an implantable nerve sensing and electrical stimulation system according to the present invention having a single nerve cuff positioned around the sciatic nerve of a patient.

In each of the embodiments shown in FIGS. 1A, 1B, and 1C, the implanted closed-loop control unit 50 is the same. The operation of the closed-loop control unit 50 can be programmed externally by a physician or a physical therapist to select the most appropriate sensing channels and stimulation channels depending on the exact orientation of the nerve cuff or cuffs and the placement of the various electrodes with respect to the nerve or nerves in relation to the individual neuroanatomical features of the patient. According to this invention the surgeon need not be concerned with installing the nerve cuff according to any particular orientation with respect to the nerve, because the identification and desired assignment of channels is accomplished by the physician or therapist after the implanted system is in place.

FIG. 2 illustrates one suitable embodiment of a multi-channel nerve cuff for use with the implantable closed-loop nerve stimulation system of the present invention. The nerve cuff 70 is a flexible, tubular structure having an opening 72 extending along its length that allows the cuff 70 to be wrapped around a nerve. The opening 72 is closable with a number of mechanisms such as a tongue and groove connector or a series of interlocking closing members having holes therein through which a suitable closing element such as a hinge pin can be received. A series of longitudinally extending ridges 74 divide the interior of the nerve cuff into a number of isolated chambers, such that each chamber surrounds a different portion of the exterior of the nerve. Within each chamber are a number of electrodes that comprise small wires that are in the vicinity of nerve fibers when the cuff is closed. Preferably, for the purpose of sensing the very small nerve signals while rejecting the much larger electromyographic potentials generated by neighboring muscles and other common mode noise produced by sources outside the cuff, the electrodes inside each nerve cuff chamber are connected in a balanced tripolar configuration wherein each recording electrode is placed in the middle of the cuff and an indifferent electrode pair is symmetrically disposed near the edges of the cuff, the recording and indifferent electrodes having separate conductive leads. Thus, one lead terminates at a sensing electrode positioned at the center of the cuff and the other lead terminates in a pair of electrodes that are positioned proximal and distal to the sensing electrode in the same chamber of the nerve cuff. A common ground electrode extends around a portion of the exterior proximal and distal ends of the nerve cuff to provide a reference voltage and to further reduce common mode noise caused by musculature and other sources located outside the nerve cuff.

Figure 3:
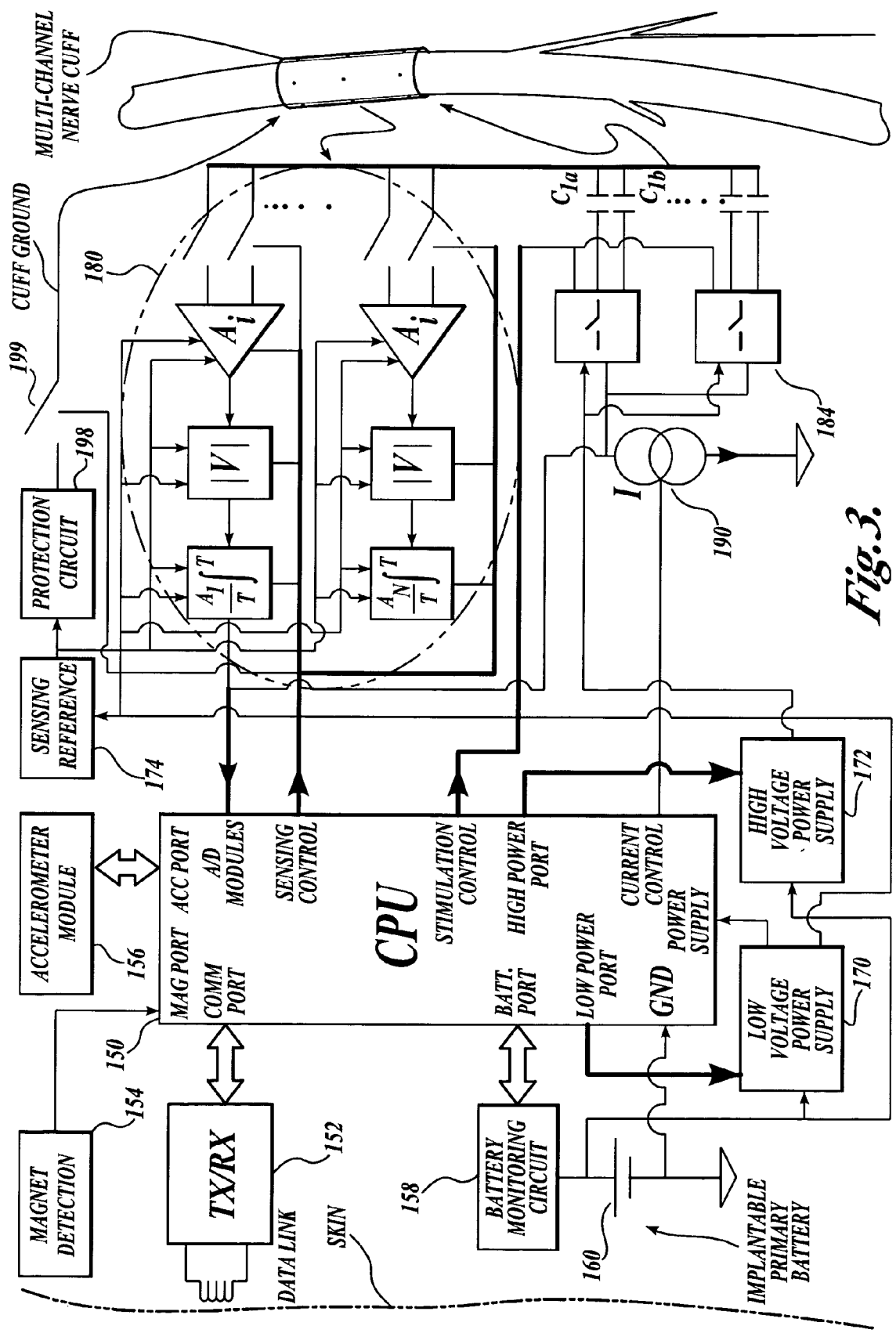
FIG. 3 is a block diagram of an implantable closed-loop nerve signal sensing and electrical stimulation system for treating foot drop in accordance with one embodiment of the present invention.

A block diagram of an implantable nerve stimulation system in accordance with one embodiment of the present invention is shown in FIG. 3. The closed-loop control unit 50 includes a programmable processor 150, which in a preferred embodiment includes two low power, 8-bit PIC microcontrollers, such as model numbers 18C452 and 16C673, available from Microchip. The closed-loop control unit 50 consumes a maximum of 22.4 milliwatts during operation. The processor 150 is interfaced with a number of other circuit components including a wireless receiver/transmitter 152, a magnet detector 154, an accelerometer circuit 156, and a battery monitoring circuit 158.

The wireless transmitter/receiver 152 allows the processor 150 to communicate with an external controller (shown in FIG. 4) that is positioned outside the body in order to program the operation of the nerve signal sensing and stimulation systems as well as to transfer programmed data to the external controller.

The magnet detector 154 detects the presence of an external magnet (shown in FIG. 4) that is placed on the skin of the patient in order to allow the user or physical therapist to select different modes of operation of the device, as will be explained below.

The accelerometer circuit 156 provides signals from a pair of orthogonally oriented accelerometers that are used to determine the angle of the patient's thigh. Signals from the accelerometer circuit 156 are used to determine if the patient is standing and what type of stimulation signals should be provided to the muscles depending upon whether the patient is walking on a level surface or up/down a set of stairs.

A long life battery, such as a lithium battery 160, provides power to the processor 150 and other peripherals of the closed-loop nerve stimulation system. The battery 160 is connected to the battery monitoring circuit 158 that provides the processor 150 with a signal that is indicative of the expected life of the battery 160. The closed-loop control unit 50 also includes a low voltage power supply 170 and a high voltage power supply 172. The low voltage power supply 170 supplies power to the processors 150, to a bank of amplifiers and signal conditioning circuits 180 that amplify and condition the nerve signals sensed by the electrodes in a nerve cuff, as well as to a voltage reference circuit 174. The high voltage power supply 172 supplies power to a bank of stimulation circuits 184 that deliver stimulation pulses to the electrodes in the nerve cuffs.

There are N signal conditioning circuits of which one or more are selected to detect the HC and TL events. The number of signal conditioning circuits used and which electrodes they are connected to are programmable by the doctor or the physical therapist.

Figure 4:
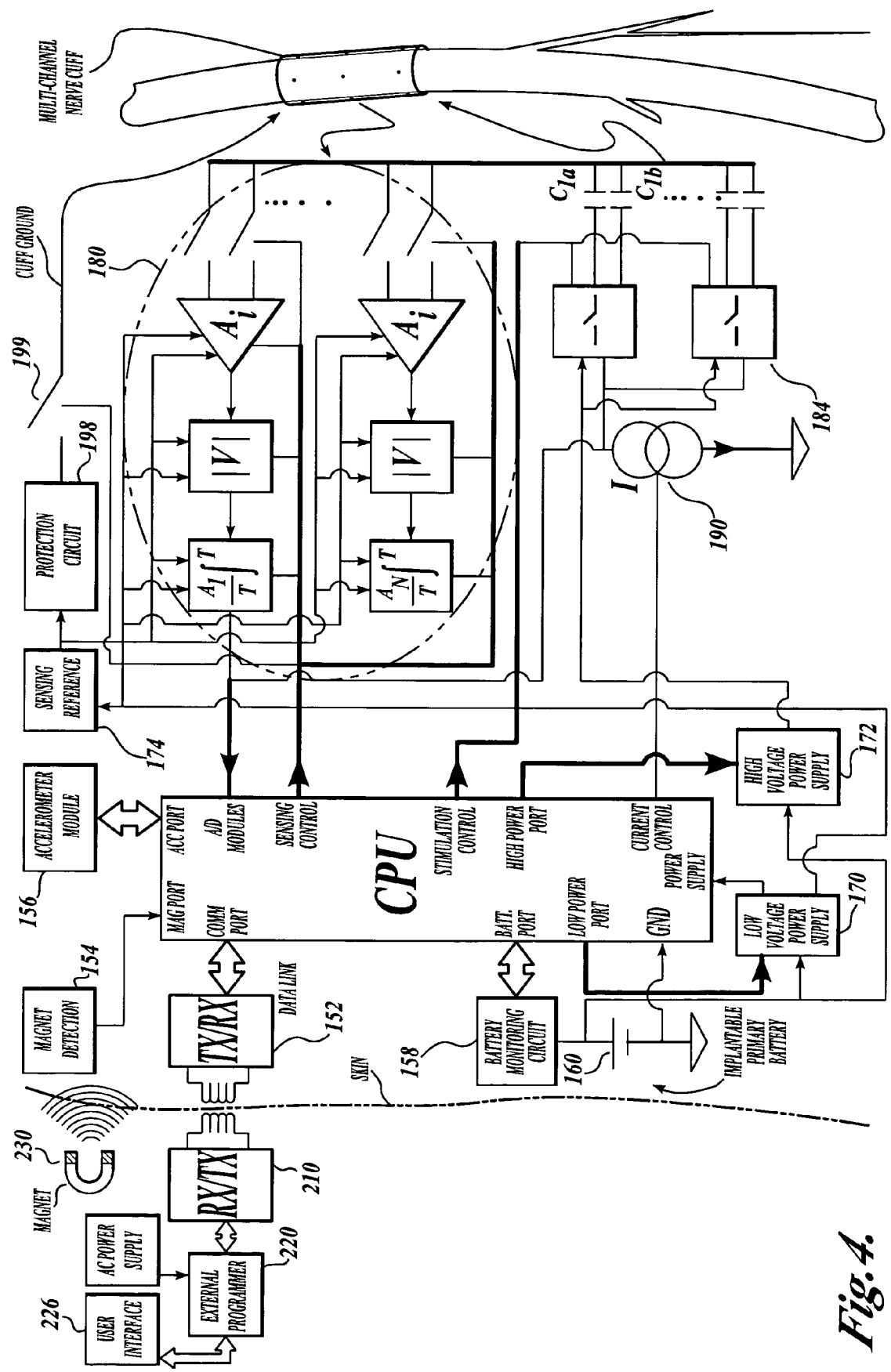
FIG. 4 illustrates how the implantable closed-loop nerve signal sensing and electrical stimulation system shown in FIG. 3 is programmed with external components.

FIG. 4 illustrates the implantable closed-loop nerve stimulation system in communication with an external device that includes a wireless receiver/transmitter 210, an external programmer 220 and a user interface 226. The wireless receiver/transmitter 210 communicates with the corresponding wireless transmitter/receiver 152 that is within the closed-loop control unit 50 via a transcutaneous, inductive-coupled radio frequency (RF) signal. Suitable wireless receiver/transmitter communication circuits are custom designed for each application and their use is considered well known to those of ordinary skill in the art. The wireless transmitter/receiver pair 152, 210 transmits at a sufficiently low power to allow communication between the processor 150 and the external programmer 220 with negligible heating of the titanium enclosure of the closed-loop control unit.

The external programmer 220 and a user interface 226 are used by a physician or physical therapist to tune the operation of the implanted closed-loop nerve stimulation system. The wireless receiver/transmitter 210 is coupled to the external programmer 220 and user interface 226 residing in a battery powered laptop or other computer, such as a personal digital assistant (PDA), in order to allow a physician or physical therapist to program the closed-loop nerve stimulation system after it has been implanted inside the patient. The external programmer 220 can vary a number of programmable parameters including how many signal conditioning circuits are used to detect event signals from the nerve fibers and which electrodes each of the selected signal conditioning circuits is connected to. Similarly, which electrodes should receive the stimulation pulses and the pattern of stimulation can be adjusted to better control movement of the foot during the swing phase of walking by the patient.

A magnet 230 can be placed on the patient's skin in the vicinity of the implanted closed-loop control unit 50 to trigger the magnet detector 154 in order to change the operation of the processor 150. The magnet detector 154 preferably comprises a reed switch or other magnetically activated component that detects the proximity of the magnet 230.

As will be explained in further detail below, the closed-loop control unit 50 is designed to operate with very low power consumption such that for the embodiment in FIG. 3, the primary battery 160 that powers the device will last an average of four to six months before needing to be replaced. It is anticipated that advances in battery technology may further increase the expected primary battery life.

In some instances, it may be desirable to power the implantable closed-loop nerve stimulation system with a rechargeable, or secondary, battery. In the embodiment shown in FIG. 5, the closed-loop nerve stimulation device includes a rechargeable battery 250, such as a lithium-ion battery. A battery management circuit 252 is coupled to the processor 150 and alerts the processor when the battery power is approaching minimal levels. The rechargeable battery 250 is preferably inductively charged, from an external power supply via an external antenna 258 that is placed outside of the patient close to the skin overlying the implanted closed-loop control unit 50. Because the power of the RF signals used to charge the battery may heat the metal enclosure that houses the closed-loop control unit 50, the internal power link antenna 259 is preferably located in a separate header (not shown) outside the metal housing that surrounds the closed-loop control unit. RF power supplied by an external inductive energy transfer module 260 to the internal antenna 259 is rectified by a rectifier circuit 256 that is coupled to the battery management circuit 252 in order to charge the battery 250. To avoid the enclosure of the closed-loop control unit 50 from exceeding a maximum allowed temperature, a temperature sensor 261 is provided in the closed-loop control unit 50 to monitor the temperature of the device. If the device temperature reaches a specified value, the processor 150 immediately halts the battery charging process until the temperature has returned to safe levels.

On the outside of the body, the external inductive energy transfer module 260 is positioned adjacent to the power link receiving antenna 259 that is inside the body. The electromagnetic energy delivered by the inductive energy transfer module 260 is received from an external charging circuit 262 which in turn is powered by a rechargeable battery pack 264. Therefore, the user can recharge the battery of the implanted closed-loop nerve stimulation system at any convenient time and location.

Each of the amplifiers $A_i$ within the signal conditioning circuits 180 are micro-volt-level differential amplifiers with MOSFET input stages. Together with the sensing reference voltage 174 and the protection circuit 198, the amplifiers are described in U.S. patent application Ser. No. 09/988,112, titled Implantable Signal Amplifying Circuit for Electroneurographic Recording, filed Nov. 19, 2001, which is herein incorporated in its entirety by reference, but is summarized below for completeness. Each amplifier includes an extremely low DC input current MOSFET stage that serves as a first input protection circuit to limit current flow through the nerve and electrode wires. Protection circuit 198, which preferably comprises a parallel resistor/capacitor combination, provides a second input protection, in compliance with regulatory requirements, and serves to protect all amplifiers in case of any amplifier $A_i$ failure. Such protection circuit 198 does not degrade the high CMRR needed in the signal conditioning circuit 180 and reduces the implant area. Also, the extremely low DC input currents of the MOSFET stages enable recording in between stimuli using the same nerve cuff electrode that delivers the stimulation.

To be used for closed-loop control, the amplifiers $A_i$ in the bank of signal conditioning circuits 180 can be selected and programmed by the therapist using the external programmer 220 of FIG. 4. The programmer's wireless receiver/transmitter 210 transfers the data to the processor 150, via the wireless receiver/transmitter 152 of the implanted closed-loop control unit 50. The signals picked up by the sensing channels selected from among the multi-channel nerve cuff electrode, after being band-pass amplified by the amplifiers $A_i$, are full-wave rectified and bin-integrated by an integration circuit such as a -capacitor integrator. The bin time and sensing duty cycle are also selectable and programmable by the therapist, which allows a further reduction of power consumption. The bin-integrated signals are fed to analog-to-digital converter modules in the processor 150. The processor 150 processes the bin-integrated signals to detect the HC and TL events, using a morphological filter algorithm (described below), and controls the activation and connection of the signal conditioning circuits 180 and sensing reference 174 (via switch 199 as shown in FIG. 3). This control of the signal conditioning circuits 180 and sensing reference 174 by the processor 150 reduces power consumption, avoids saturation of the amplifiers $A_i$ during delivery of high-voltage stimuli, and avoids unwanted stimulation through the recording electrodes during multi-channel stimulation.

The signal conditioning circuits 180 and all power-ripple sensitive circuitry of closed-loop control unit 50, are powered by the low voltage power supply 170. The cascade of a low-input voltage, step-up DC/DC converter, and an ultra low-dropout regulator comprises the low voltage power supply 170. The processor 150 also controls the enabling of the low voltage power supply 170, further reducing power consumption.

Multi-channel cyclic stimulation of two or more electrodes in a nerve cuff is achieved by the programmable current reference 190 that is shared by all stimulation circuits. The stimulation circuits also include the low-on resistance, high-voltage switches 184, DC current blocking capacitors $C_{1a}$ and $C_{1b}$, and the high voltage power supply 172. The number of stimulation channels, stimulation currents and patterns (i.e. initial doublet or triplet, ramps, etc.) are also selectable and programmable by the therapist. The stimulation waveform applied to a nerve is preferably a rectangular pulse, with programmable width, and exponential charge recovery. The delay between the end of the stimulation pulse and the start of the recovery discharge is preferably less than 100 μs.

For nerve stimulation, each of the switches 184 in the stimulation circuits connects the series combination of a first DC current-blocking capacitor $C_{1a}$, the electrode-nerve impedance of the selected channel, and a second DC current-blocking capacitor $C_{1b}$. The double capacitor scheme provides redundancy against single failure. To deliver the stimulus, the high voltage power supply 172 is connected to the free terminal of the first capacitor $C_{1a}$, whereas the terminal of the programmable current reference 190 is connected to the free terminal of the second capacitor $C_{1b}$. Charge recovery is performed by short-circuiting the terminals of the first and second capacitor. The switches 184 also perform this action at times that are controlled by the processor 150.

The programmable current reference 190 is also used for impedance measurements. When this measurement is requested by the therapist via the external programmer 220, the processor 150 sends two or more sub-threshold stimulation pulses and measures the voltage drop between the high voltage power supply 172 and the terminal of the programmable current reference 190 for each-pulse. These values are then sent back to the external programmer 220, where the complex impedance is automatically calculated using the measured values. This method of measuring impedance gives equivalent results to and avoids the need for a sinusoidal signal generator inside closed-loop control unit 50, which is traditionally used for nerve cuff electrode impedance measurements.

A programmable, low-input voltage, step-up DC/DC converter, composes the high voltage power supply 172. Its output voltage can be selected and programmed based on the stimulation current value needed for muscle recruitment and the measured impedance of the electrode-nerve interface. This feature allows reduction of power consumption during stimulation.

Figure 5:
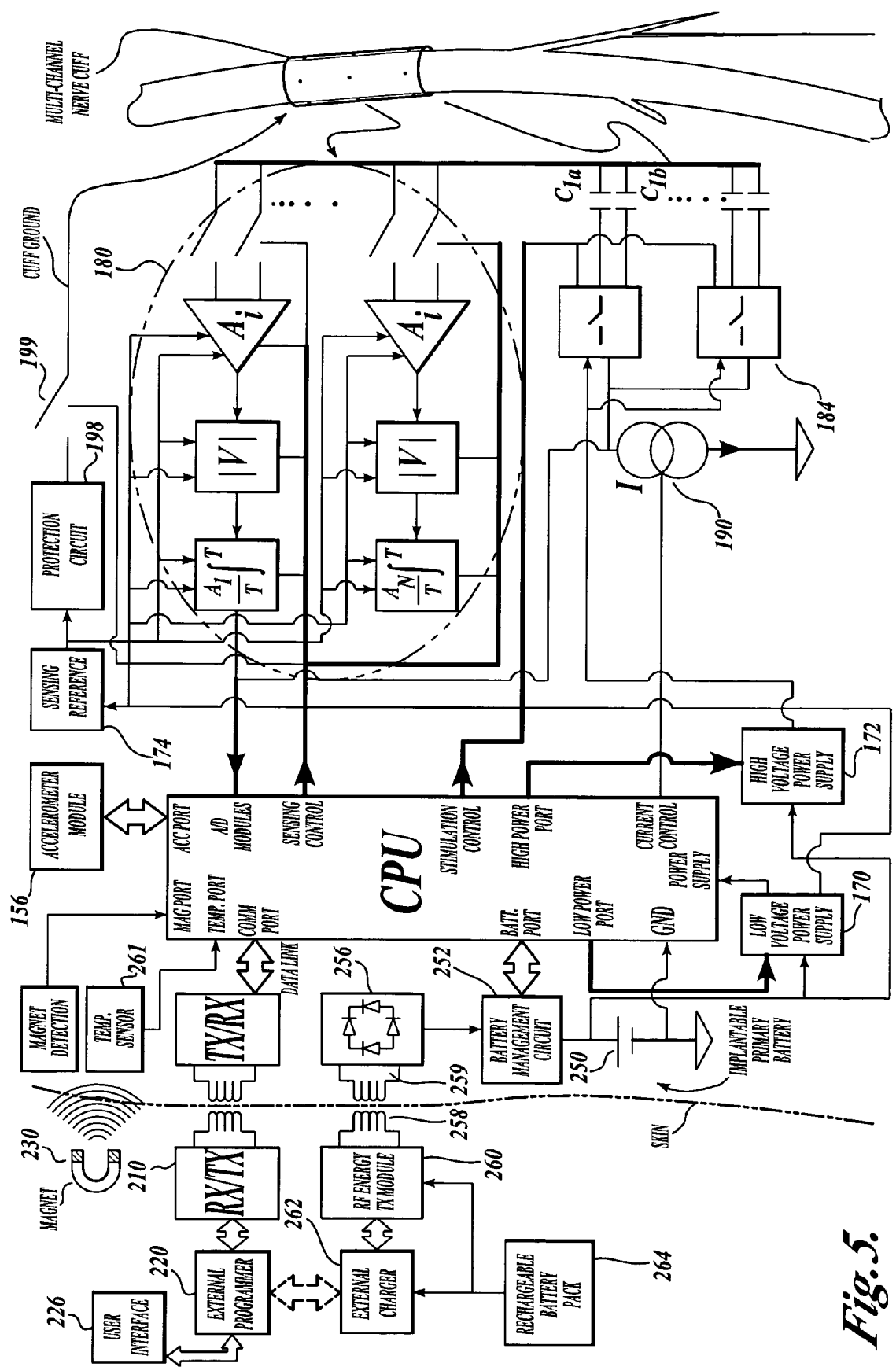
FIG. 5 illustrates an embodiment of an implantable closed-loop nerve signal sensing and electrical stimulation system that is powered by a rechargeable battery according to the present invention.

The processor 150 can also execute a therapist-programmable, therapeutic stimulation exercise program, which can be activated/deactivated by the patient using the external magnet 230 (see FIG. 5). This stimulation exercise program allows the subject to increase the strength, blood flow and neuro-motor robustness of the affected muscles distal to the implanted nerve cuff electrodes, without having to walk and in the comfort of their own home. The magnet can also be used to send the processor 150 to OFF state, which provides a safety feature in case the communication with the implanted closed-loop control unit fails.

The closed-loop control unit 50 has two states of operation: OFF and ON. While the control unit 50 is in the OFF State, it only attempts to communicate with the external programmer 220 once every second. The OFF state is the default state. The ON state, on the other hand, is further divided into SLEEP, READY, WALKING, STAIR-ASCENT, STAIR-DESCENT, and MAGNET OFF/EXERCISE modes. As a safety feature, the control unit 50 switches to the OFF state from any other mode if the battery voltage read by the battery monitoring circuit 158 is lower than a certain pre-defined value. Only interrogation and programming orders are executable in OFF State.

While the closed-loop control unit 50 is operating in the ON state, it automatically switches among the various operating modes depending on the sensed signals used for closed-loop control. These signals are the thigh angle measured by the accelerometer 156, the foot contact events detected by the processor 150 and the bank of signal conditioning circuits 180, and the presence of a magnet 230 as detected by the magnet detection circuit 154. For example, the closed-loop control unit 50 switches to SLEEP mode whenever the accelerometer module 156 indicates that the patient's thigh is not vertical. In SLEEP mode, the processor 150 turns off most of the closed-loop control unit's circuitry, thus minimising power consumption.

Upon detection that the thigh position is becoming vertical by the accelerometer circuit 156, the processor 150 "wakes up" and enters the READY mode to begin looking for physiological events, such as a toe lift (TL) event. Each signal conditioning circuit 180 is selectively coupled to an electrode in a nerve cuff by a programmable switch to scan for nerve signals indicating these events. Upon detection of one or both of these events, the processor 150 selectively enables one or more of the stimulation circuits by closing one or more switches 184 to deliver stimulation pulse(s) to the nerve fiber in order to move a muscle at the correct time in the patient's step.

In SLEEP mode all stimulation and sensing circuits are disabled. The closed-loop control unit 50 checks the magnet presence every second and the thigh angle every two seconds. If the magnet is detected for more than 10 seconds, the closed-loop control unit 50 switches to EXERCISE mode. If the magnet is detected for more than 3 seconds, it switches to OFF (Magnet OFF mode). It switches to READY mode when the thigh angle is vertical.

In EXERCISE mode the control unit stimulates with the programmed exercise pattern for 10 minutes or until the magnet is applied.

In READY mode the closed-loop control unit checks the thigh angle and switches back to SLEEP mode if it is not vertical. The sensing circuits are activated and the signal from the selected nerve to detect a TL event is sensed and processed using the event detection algorithm described. If a TL event is sensed it switches to WALKING mode SWING PHASE. If more than two consecutive TL events are sensed the device switches to STAIR DESCENT mode TRANSFER PHASE.

In WALKING mode SWING PHASE, the closed-loop control unit 50 stimulates according to the stimulation pattern programmed for walking on level ground. The sensing circuits are activated and the signal from the selected nerve to detect an HC event is sensed and processed using the event detection algorithm described. If an HC event is detected, the closed-loop control unit switches to WALKING mode STANCE PHASE. If no HC event is detected, it switches back to READY mode when the programmed time-out elapses. If the thigh angle corresponds to the programmed stair ascent angle, it will switch to STAIR ASCENT mode SUPPORT PHASE when a TL event is detected or the programmed time-out elapses.

In WALKING mode STANCE PHASE, the stimulation is turned off and the TL counter is reset. If a TL event is detected it switches to WALKING mode SWING PHASE. If a TL event is not detected and the programmed time-out elapses it switches to READY mode.

In STAIR DESCENT mode TRANSFER PHASE, the closed-loop control unit stimulates according to the stimulation pattern programmed for walking down stairs. Both signals from the selected nerves to detected HC and TL events are sensed and processed. If an HC event is detected the closed-loop control unit switches to WALKING mode STANCE PHASE. If a TL event is detected it switches to STAIR DESCENT mode SUPPORT PHASE. If no HC or TL events are detected and the programmed time-out elapses the closed-loop control unit turns off the stimulation and switches to READY mode.

In STAIR DESCENT mode SUPPORT PHASE, the stimulation is turned OFF. The sensing circuits are activated and the signal from the selected nerve to detect TL is sensed and processed. If a TL event is detected the closed-loop control un it switches to STAIR DESCENT mode TRANSFER PHASE. If no TL event is detected and the programmed time-out elapses, it switches to READY mode.

In STAIR ASCENT mode SUPPORT PHASE, the stimulation is turned OFF. The sensing circuits are activated and the signal from the selected nerve to detected TL is sensed and processed. If a TL event is detected and the thigh angle corresponds to the programmed stair ascent angle, the closed-loop control unit remains in the same state. If a TL event is detected and the thigh angle does not correspond to the programmed stair ascent angle, it switches to STAIR ASCENT mode TRANSFER PHASE. If no TL is detected and the programmed time-out elapses it switches to READY mode.

In STAIR ASCENT mode TRANSFER PHASE the closed-loop control unit stimulates according to the stimulation pattern programmed for walking up stairs. Both signals from the selected nerves to detect HC and TL events are sensed and processed. If an HC event is detected, the closed-loop control unit switches to WALKING mode STANCE PHASE. If a TL event is detected and the thigh angle does not correspond to the programmed stair ascent angle, the closed-loop control unit remains in the same state. If a TL event is detected and the thigh angle corresponds to the programmed stair ascent angle it switches to STAIR ASCENT SUPPORT PHASE. If no HC or TL events are detected and the programmed time-out elapses, the closed-loop control unit turns off the stimulation and switches to READY mode.

Figure 6:
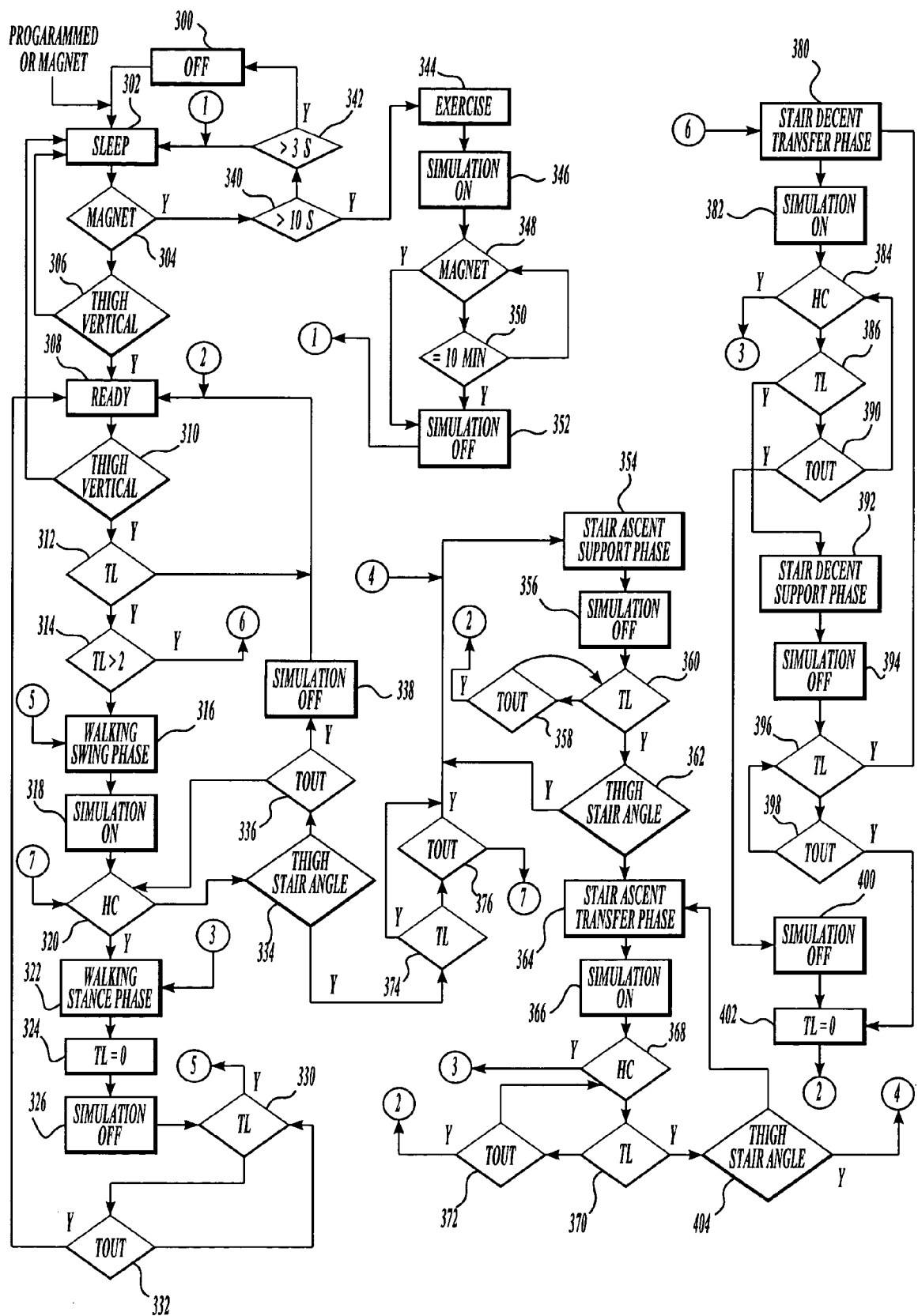
FIG. 6 is a state diagram showing the operation of one embodiment of a closed-loop nerve stimulation system according to the present invention.

FIG. 6 is a state diagram showing one possible programming implementation of the processor's operation as described above. As discussed, the processor 150 enters the OFF mode 300 when the battery level drops below a predetermined minimum or when the user has turned the device off with a magnet. At a preprogrammed ON time or when the user manually awakens the control unit with the magnet, the processor enters the SLEEP mode 302. In the SLEEP mode, the processor periodically detects for the presence of a magnet at 304. If the magnet is detected, it is determined at 340 whether the magnet has been present for more than 10 seconds. If so, the processor enters an EXERCISE mode 344, as will be described below. If the magnet has been in place for less than 10 seconds, it is determined if the magnet was in place for more than 3 seconds at step 342. If so, the processor returns to the OFF state 300. If the magnet was in place for less than 3 seconds, the processor returns to the SLEEP mode 302.

At 306, the processor determines if the thigh is oriented in a vertical direction by checking the signals from the accelerometer circuit. If so, the device enters the READY mode 308. In the READY mode, the processor begins checking the angular orientation of the thigh at more frequent intervals such as every 50 milliseconds. If the thigh is vertical, the processor checks for the presence of a toe lift event at 312. If no toe lift is detected, processor returns to the READY mode 308. If the toe lift is detected, it is determined if the toe lift time is greater than 2 seconds at 314. If so, the processor enters the STAIR DESCENT TRANSFER PHASE 380 as will be described below.

If the TL counter is less than 2 seconds, the processor enters the WALKING mode SWING PHASE 316 and begins stimulating selected nerve fibers at 318. At 320, the processor determines if there is a heel contact event. If not, the processor determines if the user's thigh angle indicates that the user is walking on a stair at 334. If not, the processor determines if a time-out event has occurred at 336. If there is no time-out, the processor returns to 320 to detect the occurrence of the next heel contact event.

Once a heel contact event is determined at 320, the processor enters the WALKING mode STANCE PHASE 322. At 324, the processor then resets a toe lift event counter and turns stimulation off at 326. The processor then determines at 330 whether a toe lift event has occurred. If not, the processor proceeds to 332 and determines if a time-out has occurred. If a time-out does occur, processor returns to the ready state 308. If a time-out has not occurred, the processor prepares to detect the next toe lift event 330. Once the toe lift event at 330 occurs, the processor proceeds to the WALKING mode SWING PHASE 316, described above. If it is determined at 334 that the thigh angle indicates that the user is on a stair, then the processor proceeds to 374 where it is determined if a toe lift event has occurred. If so, the processor proceeds to a STAIR ASCENT SUPPORT PHASE 354 and stimulation is turned off at 356 so that stimulation is not applied while the patient is supporting weight with the affected leg while standing on a stair. At 360, it is determined if a toe lift event has occurred. If not, the processor determines at 358 if a time-out has occurred until either the toe lift event at 360 occurs or the time-out occurs. If the time-out at 358 occurs, the processor returns to the READY mode 308.

Once the toe lift event at 360 is detected, the processor determines if the user's thigh indicates they are on a stair at 362. If so, the processor returns to the STAIR ASCENT mode SUPPORT PHASE 354 as indicated above. If not, the processor enters the STAIR ASCENT mode TRANSFER PHASE 364 wherein stimulation is applied at 366 until a determination is made that a heel contact event occurs at 368. If so, the processor enters the WALKING mode STANCE PHASE 322 as described above. If no heel contact event is detected at 368, it is determined at 370 whether a toe lift event has occurred. If no toe lift is detected at 370, it is determined if a timer has expired at 372. If not, the processor determines again if a heel contact event occurs at 368. If the timer checked at 372 has timed out, the processor returns to the READY mode 308. If a toe lift event occurs at 370, it is determined whether the thigh indicates that the user is standing on a stair at 404. If so, the processor enters the STAIR ASCENT SUPPORT PHASE 354 described above. If the thigh angle indicates that the user is not standing on a stair, the processor returns to the STAIR ASCENT TRANSFER PHASE 364 described above.

If the toe lift counter has a duration that is greater than 2 seconds, then the processor enters the STAIR DESCENT TRANSFER PHASE 380, wherein stimulation is applied at 382 and the processor determines if a heel contact event occurs at 384. If a heel contact event does occur, the processor enters the WALKING STANCE PHASE 322. If no heel contact event is detected at 384, the processor determines if a toe lift event occurs at 386. If so, the processor enters the STAIR DESCENT SUPPORT PHASE 392. If no toe lift event at 386 is detected, the processor determines if a time-out occurs at 390. If so, processor enters the READY MODE. If not, the processor returns to detect a heel contact event at 384. If a time-out does occur at 390, the processor turns off the stimulation at 400 and resets the toe lift counter to zero at 402 and returns to READY mode 308.

In the STAIR DESCENT SUPPORT PHASE 392, the stimulation is turned off at 394 and the processor determines if a toe lift event occurs at 396. If so, the processor returns to STAIR DESCENT TRANSFER PHASE 380. If not, the processor determines if a time-out has occurred at 398. If a time-out at 398 does occur, the processor resets the toe lift counter to zero at 402 before returning to the READY mode 308.

As indicated above, the user may desire to operate the nerve stimulation system in an EXERCISE mode by placing the magnet over the control unit for greater than 10 seconds. If detected at 340, the processor enters the EXERCISE mode 344 and turns stimulation on at 346. The presence of the magnet is detected at 348. If no magnet is detected, it is determined if the stimulation has been proceeding for 10 minutes at 350. If not, the processor returns to 348 to detect the presence of the magnet. If either the magnet is present or the stimulation has been proceeding for 10 minutes, stimulation is turned off at 352 and the processor returns to the SLEEP mode 302.

As indicated above, the present embodiment of the closed-loop nerve stimulation system uses two low-power microcontrollers and signal conditioning circuits to detect both when the patient is standing or walking and what type of stimulation patterns should be applied to the nerve fibers, while simultaneously aiming to minimize battery use. To detect the occurrence of a toe lift or heel contact event, the processor executes a toe lift and heel contact detection algorithm described below. The goal of the detection algorithm is to detect a HC or a TL event by processing the amplified, rectified and bin-integrated nerve signal acquired from the tibial or common-peroneal nerve when the embodiments in FIG. 1A or 1B are used, or alternatively from the sciatic nerve when the embodiment in FIG. 1C is used.

A HC or TL event in the amplified, rectified and bin-integrated nerve signal from the tibial or the common peroneal nerve is characterized by a rising or a falling trend of a certain duration and amplitude. On the other hand, this signal may also contain noise consisting of positive or negative spikes that could be of higher amplitude but of shorter duration than the event to be detected.

Figure 7A:
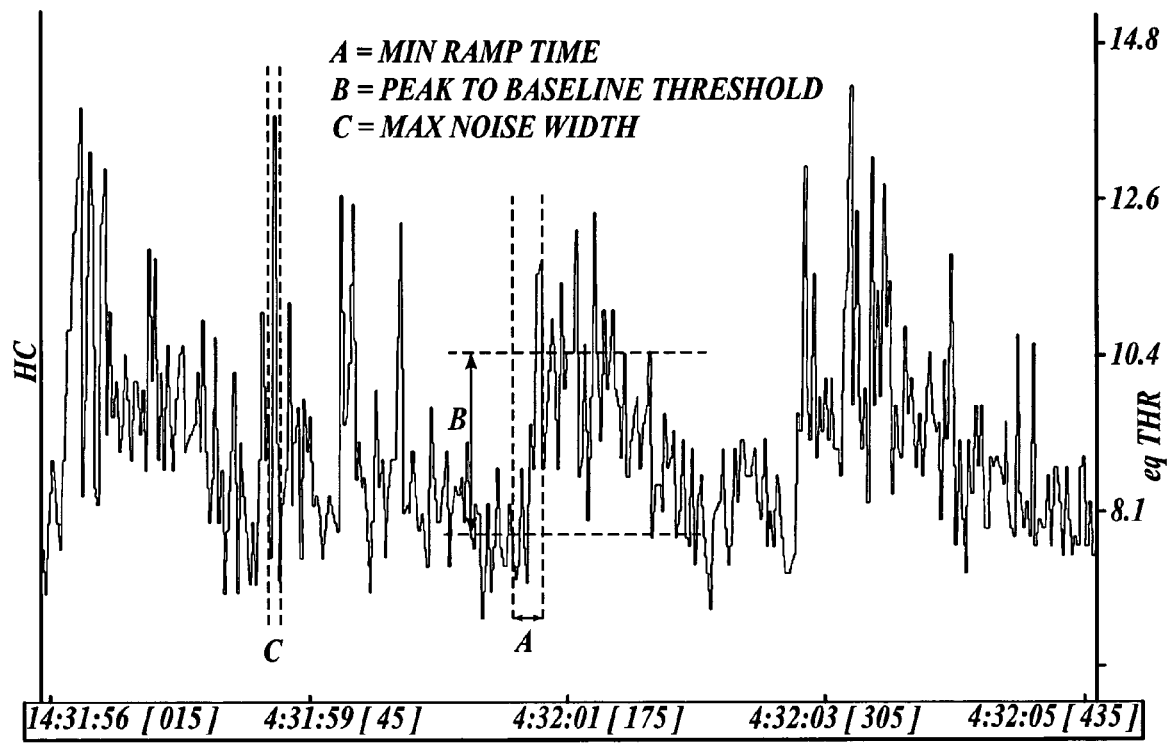
FIGS. 7A and 7B illustrate representative processed nerve signals containing heel contact and toe lift event information.
Figure 7B:
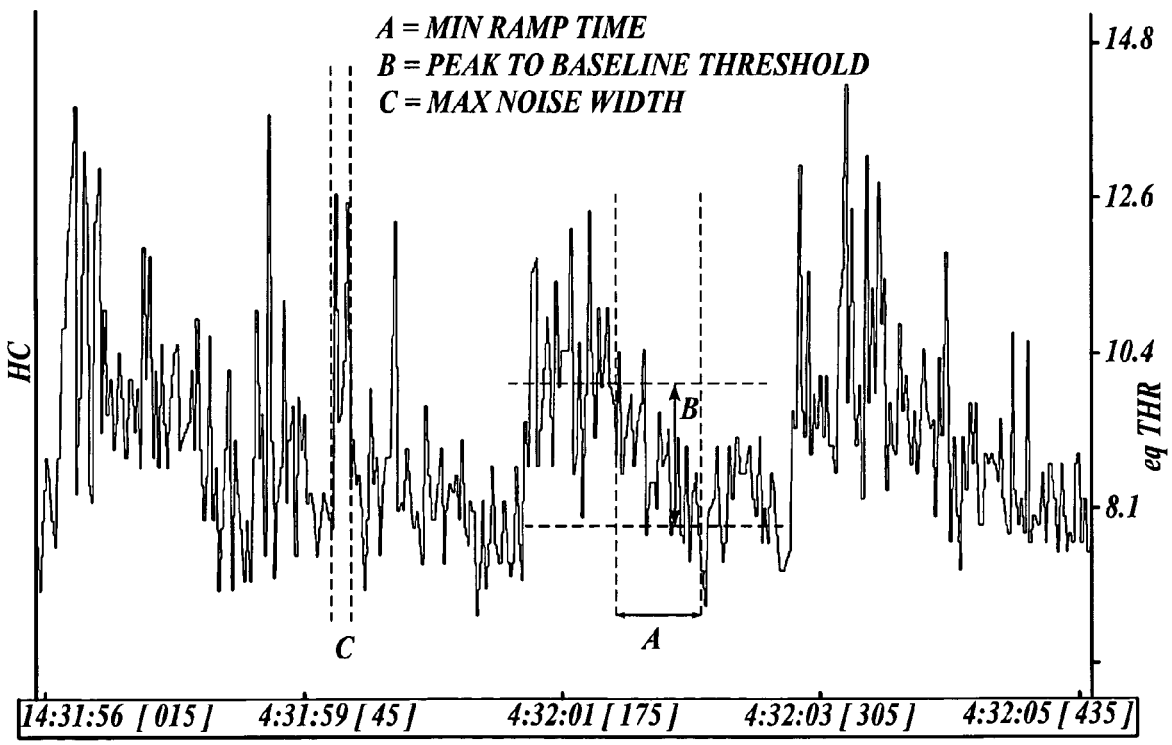

FIGS. 7A and 7B illustrate representative, processed nerve signals that are analyzed by the processor 150 for the presence of the heel contact (FIG. 7A) and toe lift (FIG. 7B) events.

An HC event can be characterized as:

a positive ramp longer than a given Minimum Ramp Time, shorter than a given Maximum Ramp Time and a peak-to-baseline difference bigger than a given Threshold. At the same time, negative spikes shorter than a given Maximum Noise Width are ignored;

or:

a negative ramp longer than a given Minimum Ramp Time, shorter than a given Maximum Ramp Time and a peak-to-baseline difference bigger than a given Threshold. At the same time, positive spikes shorter than a given Maximum Noise Width are ignored.

A TL event can be characterized as:

a positive ramp longer than a given Minimum Ramp Time, shorter than a given Maximum Ramp Time and a peak-to-baseline difference bigger than a given Threshold. At the same time, negative spikes shorter than a given Maximum Noise Width are ignored;

or:

a negative ramp longer than a given Minimum Ramp Time, shorter than a given Maximum Ramp Time and a peak-to-baseline difference bigger than a given Threshold. At the same time, positive spikes shorter than a given Maximum Noise Width are ignored.

Typically, a HC event is characterized by a positive ramp lasting 50 to 150 milliseconds and a TL event is characterized by a negative ramp lasting 150 to 300 milliseconds.

User selectable/automatic parameters of the event detection algorithm for each event are:

Ramp Type: {Rising; Falling; OFF}. This parameter is used to define the signal trend that characterizes the event, a rising or a falling ramp. In OFF the signal will not be processed.

Peak-to-baseline Threshold:{1 to 64}. It is the Signal-Peak-to-Baseline level that must be achieved to detect the event.

Min Ramp Time: {(4 to 35 samples)*sensing period ms}. Defines the minimum rising or falling time in milliseconds that characterizes the event.

Max Ramp Time: {(5 to 255 samples)*sensing period ms}. Defines the maximum rising or falling time in milliseconds that characterizes the event.

Noise Width: {(3 to 6 samples)* sensing period ms}. Defines the maximum width of the spikes to be considered as noise. Noise spikes will be negative for Rising Ramp Type and Positive for Falling Ramp Type.

Filter Order: Defines the kernel size, 3 to 6 samples, of the morphological filter.

Bin: {1 to 20 ms} Defines the Bin-integration time.

Sensing period: {15, 20, 25, 30 ms}.

The amplified, rectified and bin-integrated nerve signal acquired from the tibial or common peroneal nerves is filtered with a morphological filter that is implemented by the processor 150 according to the following expression:

$$\text{Filter}(f,B) = \gamma(\phi(f,B),B) \quad (1)$$

where $$\gamma(f,B) = \delta(\epsilon(f,B),B) \quad (2)$$

$$\phi(f,B) = \epsilon(\delta(f,B),B) \quad (3)$$

where $$\epsilon(f,B) = \min_{y \in B} f(y) \quad (4)$$

$$\epsilon(f,B) = \max_{y \in B} f(y) \quad (5)$$

where:

f is the amplified, rectified and bin-integrated signal
B is the structuring element of the filter, which size is equal to the programmed filtered order value.

When searching for a rising event, the filtered signal (out) is compared to the original signal (f) according to:

$$\text{out} = f - \text{Min}(\text{Filter}(f,B),f) \quad (6)$$

When searching for a falling event, the filtered signal is compared to the actual signal (f) according to:

$$\text{out} = \text{Max}(\text{Filter}(f,B),f) - f \quad (7)$$

Figure 7C:
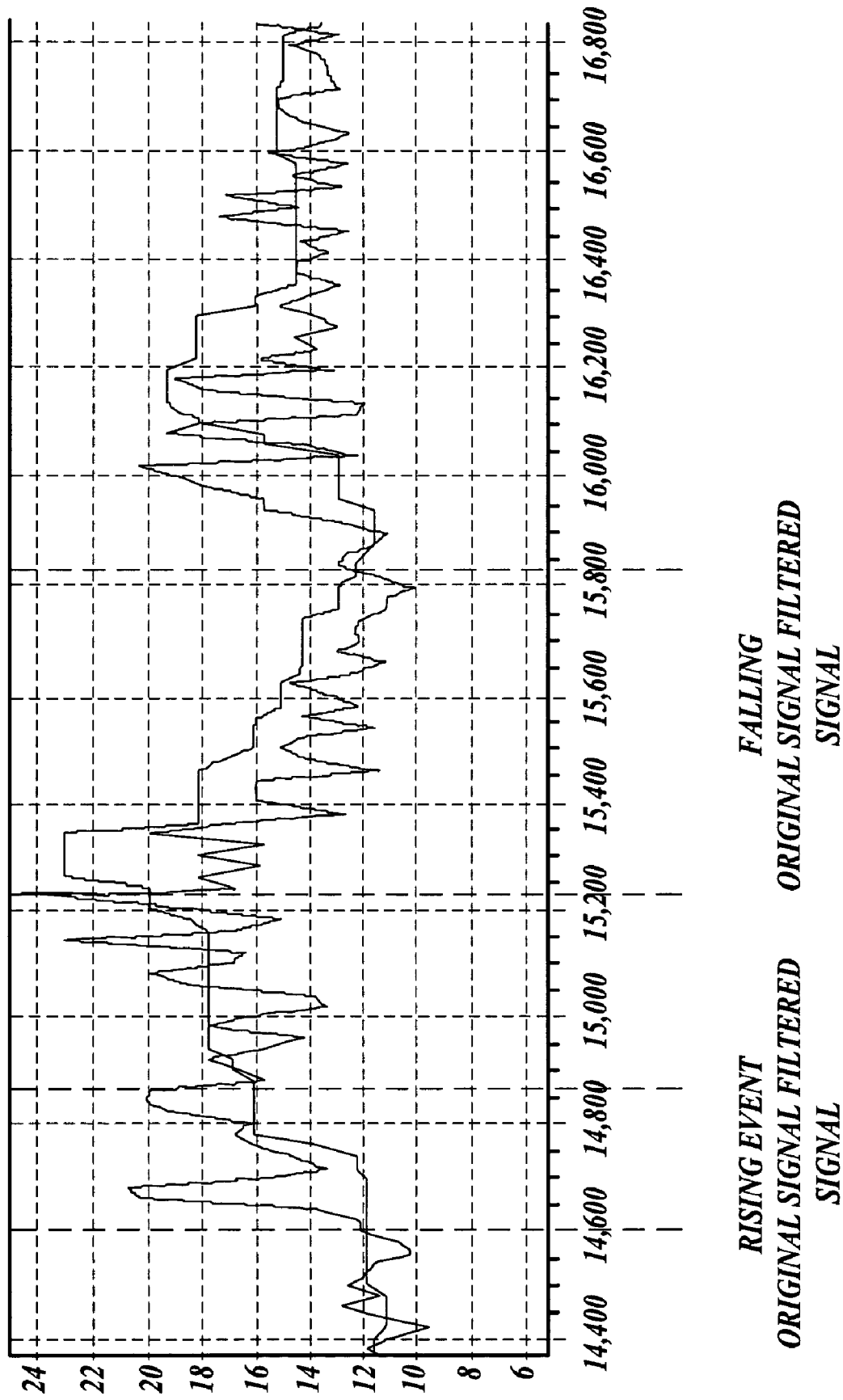
FIG. 7C illustrates a processed nerve signal and a filtered nerve signal.

FIG. 7C shows examples of an original amplified, rectified and bin integrated nerve signal and the corresponding filtered signal that is filtered with the morphological filter. As can be seen, the filter signal has a magnitude that is generally smaller than the unfiltered signal during a rising event and is generally larger than the unfiltered signal during a declining event.

Figure 8A:
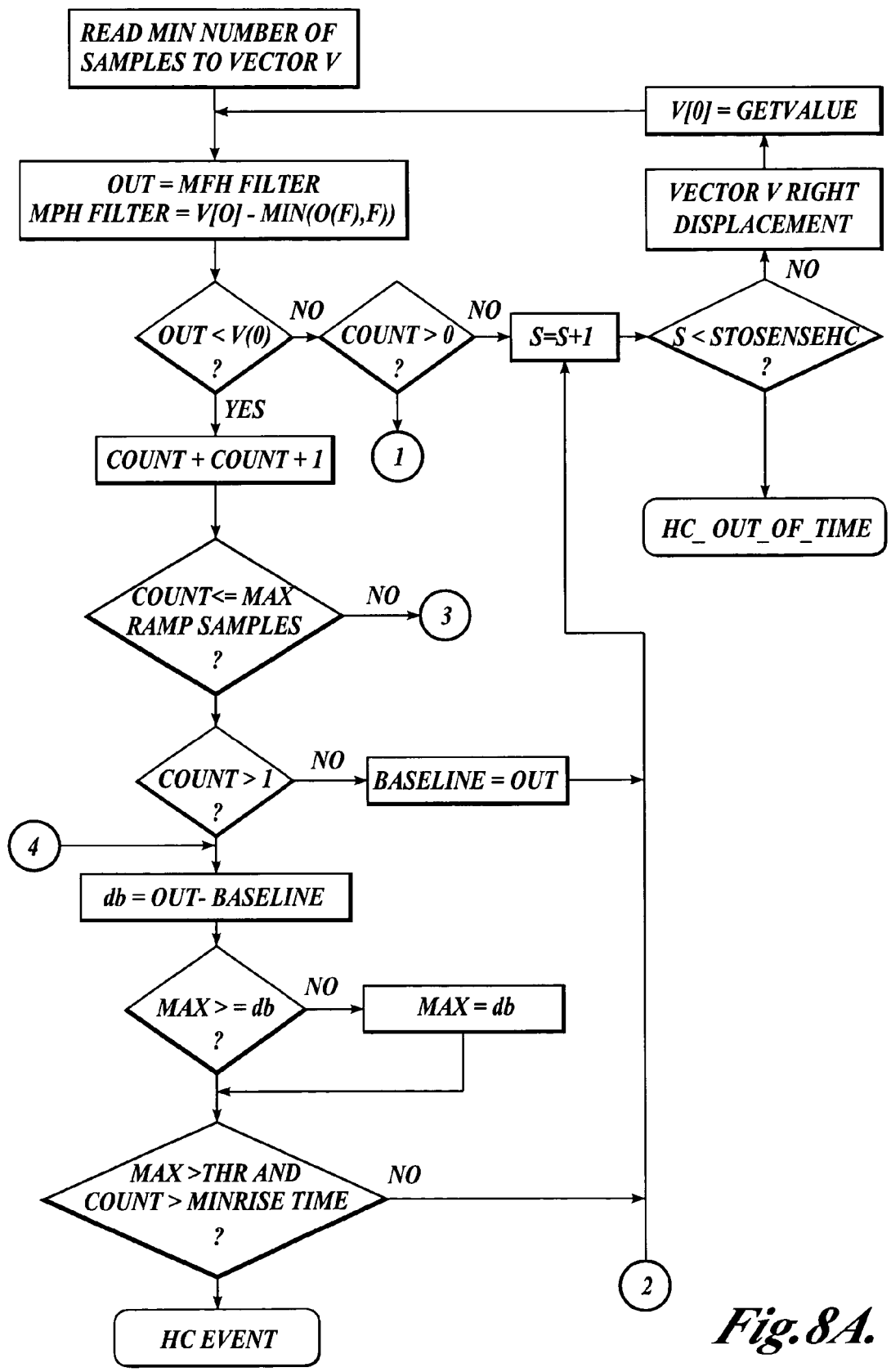
FIGS. 8A and 8B are flow diagrams of one embodiment of a heel contact event detection algorithm according to the present invention.
Figure 8B:
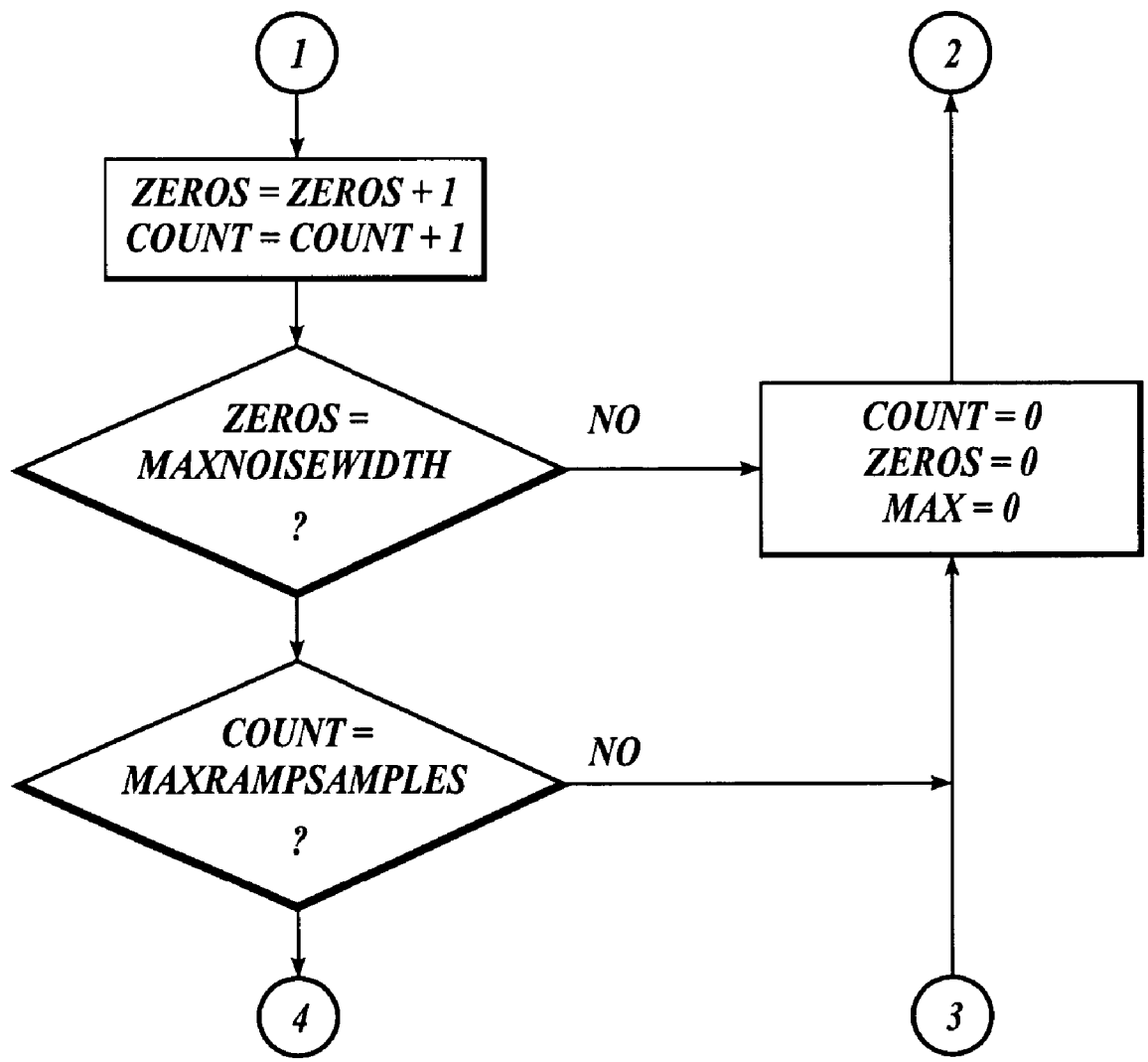

The algorithm to detect a rising event is described in FIG. 8A and FIG. 8B. As described, each acquired signal sample is filtered according to equation (1) and the result is compared with the original signal according to equation (6). If the filtered signal is lower than the original signal for a period of time >=Minimum Ramp Time and the maximum peak-to baseline difference for that period is >=Threshold, the algorithm will return a logic 1. It will return a logic 0 otherwise. At the same time, during the time period where the filtered signal is lower than the original signal, negative spikes (filtered signal higher than original signal) will be ignored if their duration is <Max Noise Width. If any of those noise spikes is longer than Max Noise Width, the filter is reset.

Figure 9A:
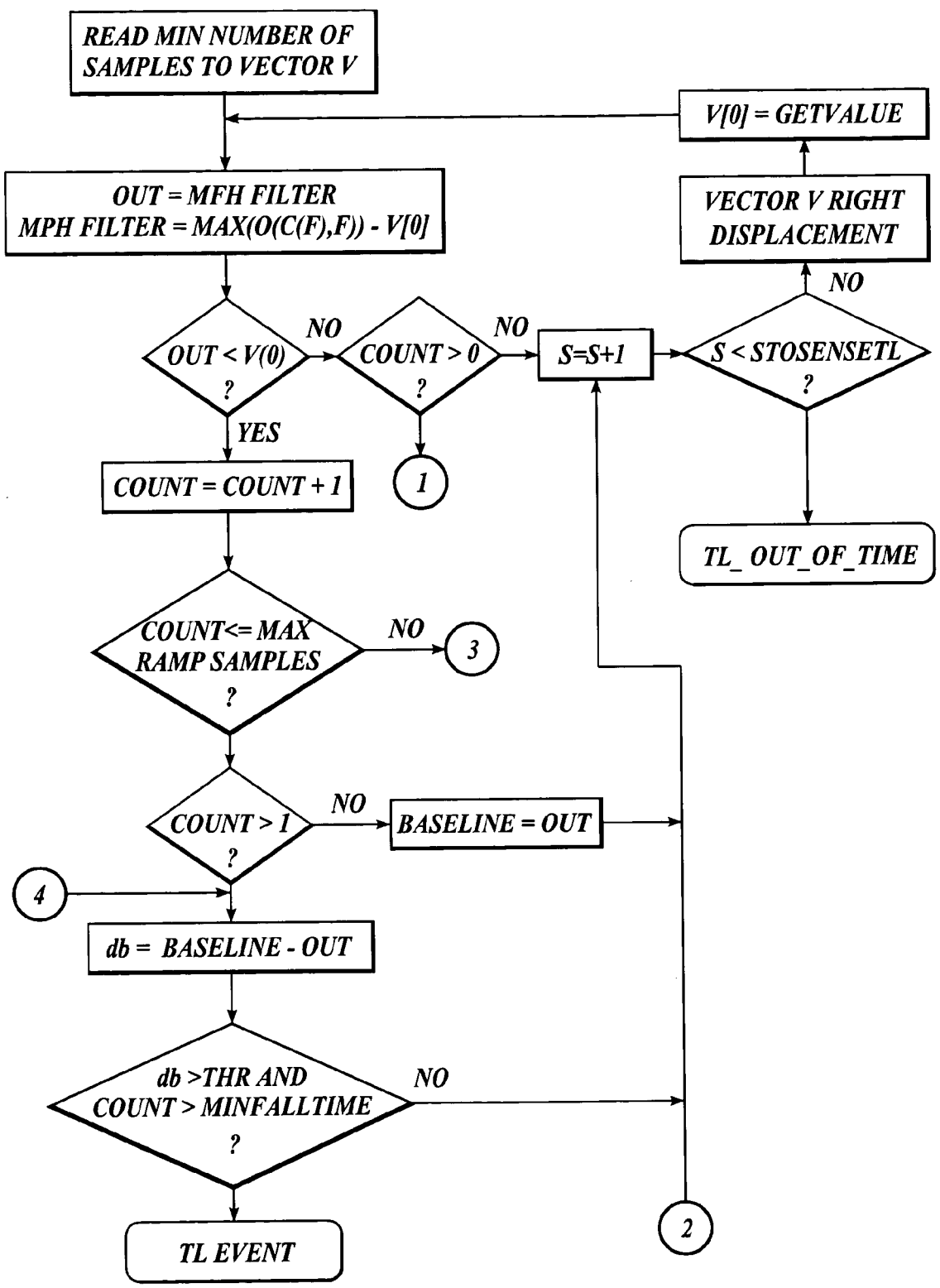
FIGS. 9A and 9B are flow diagrams of one embodiment of a toe lift event detection algorithm according to the present invention.
Figure 9B:
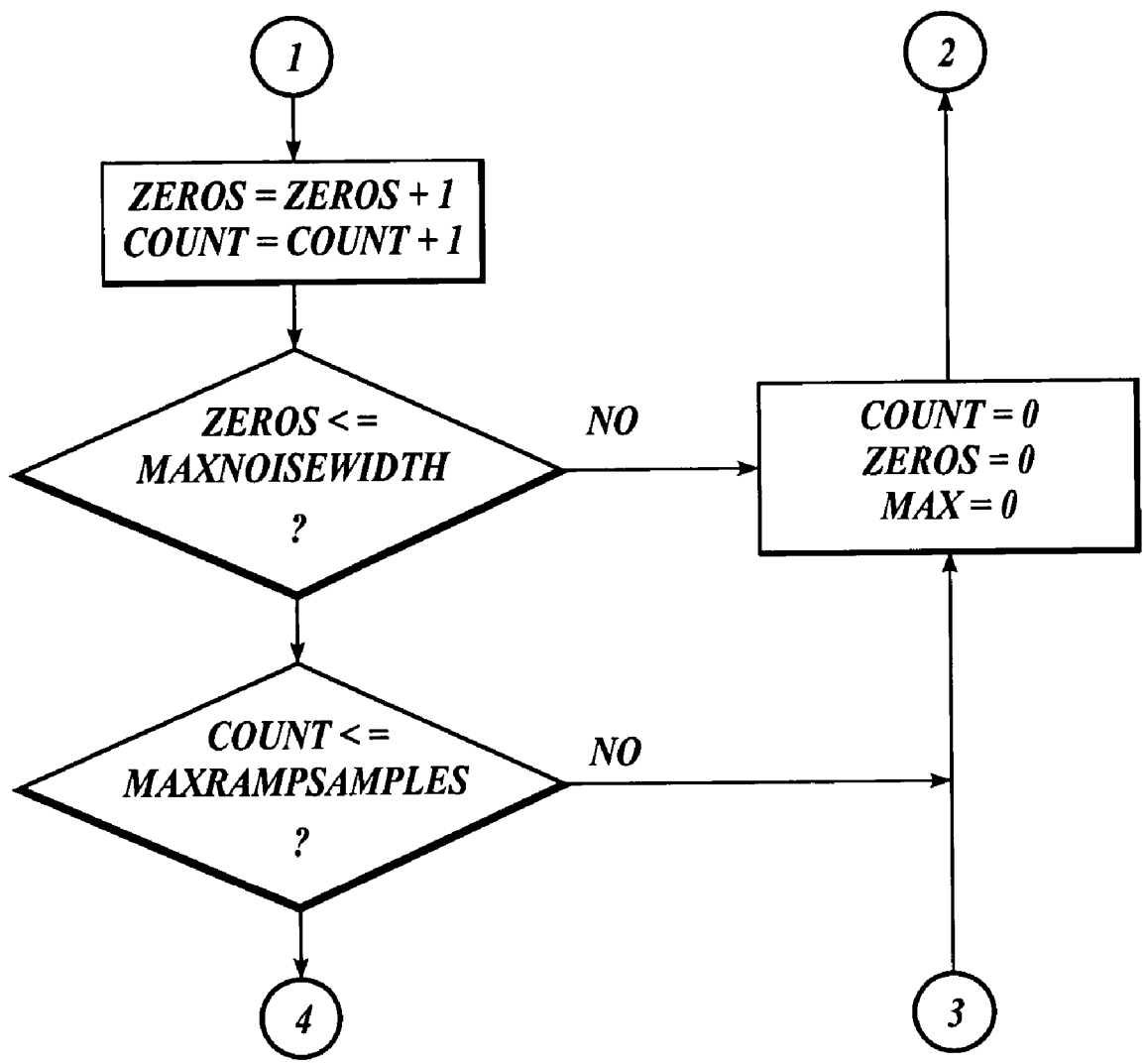

The algorithm to detect a falling event is described in FIG. 9A and FIG. 9B. As described, each acquired signal sample is filtered according to equation (1) and the result is compared with the original signal according to equation (7). If the filtered signal is higher than the original signal for a period of time >=Minimum Ramp Time and the current peak-to baseline difference >=Threshold, the algorithm will return a logic 1. It will return a logic 0 otherwise. At the same time, during the time period where the filtered signal is higher than the original signal, positive spikes (filtered signal lower than original signal) will be ignored if their duration is <Max Noise Width. If any of those noise spikes is longer than Max Noise Width, the filter is reset.

The present embodiment of the invention uses a morphological filter because such a filter does not require complicated mathematical operations or sophisticated computing power. However, other filters meeting these same requirements, such as an averaging filter, may also be used.

FIGS. 10A-10F illustrate further detail of one embodiment of an implantable band-pass amplifier of a closed-loop nerve stimulation system of the present invention; The amplifier includes built-in protection circuitry to prevent damage to the nerve in the event of a failure of a component within the implanted closed-loop control unit 50.

Figure 10A:
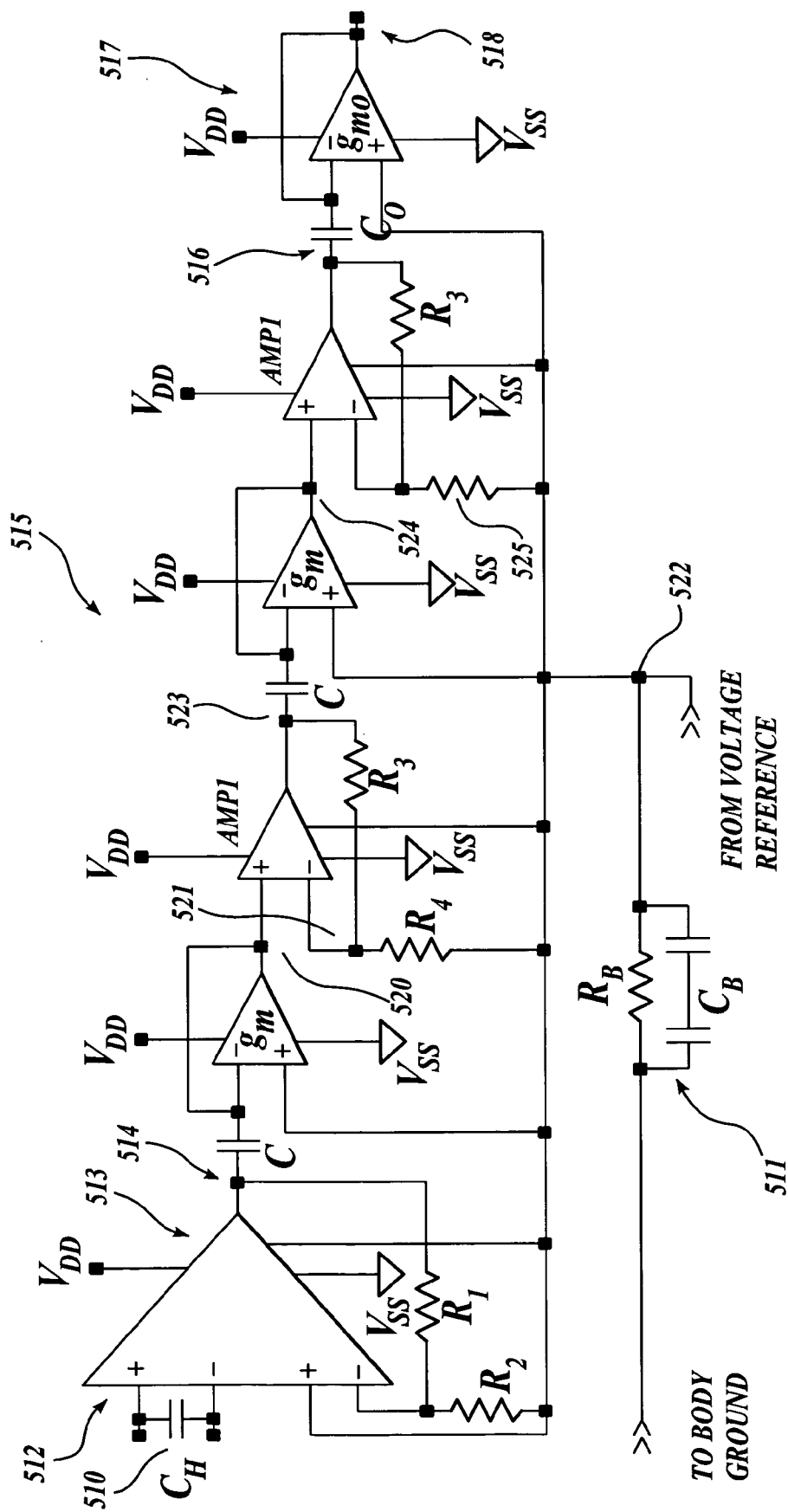
FIGS. 10A-10D illustrate an embodiment of a low-power amplifier circuit for use with the implantable closed-loop nerve signal sensing and electrical stimulation system of the present invention.

As shown in FIG. 10A, protection circuitry 511' comprises a high-value resistor $R_B$ in parallel with a series of capacitors $C_B$. Protection circuitry 511' minimizes any DC current flow caused by a semiconductor failure in preamplifier 513. Capacitors $C_B$ are selected to minimize RF noise. In case of a semiconductor failure, protection circuit 511' reduces the DC current flow below an acceptable threshold.

In preferred embodiments, the band-pass amplifier has a single-ended output architecture. While a differential output can be used in the context of the invention and may provide enhanced performance, significant area and power penalties must be paid to achieve those benefits.

Figure 10B:
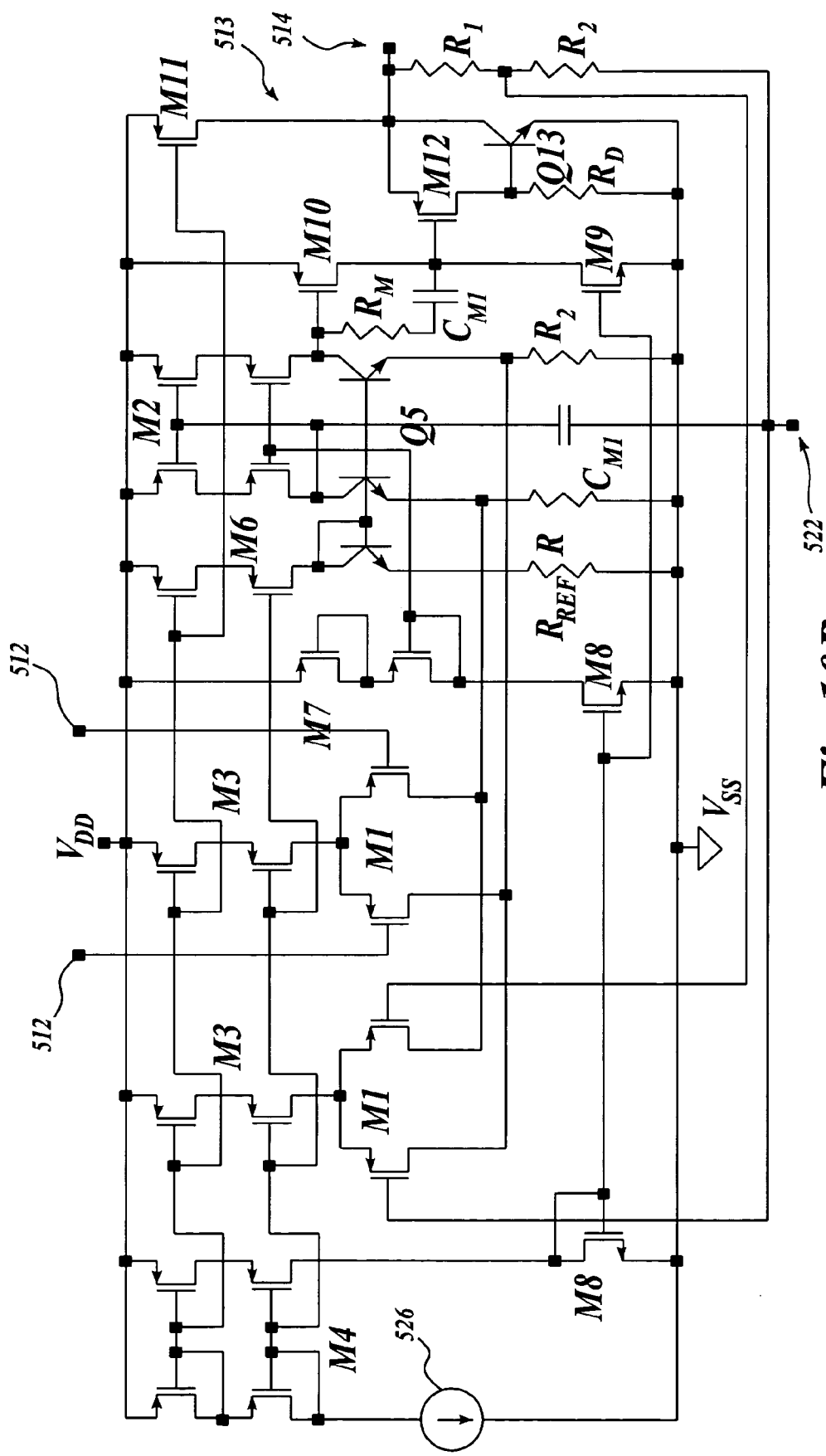

Gain programmability may be achieved, as shown in FIG. 10B, by using switches that select different combinations of resistors to vary the ratios of R3 to R4. The gain of preamplifier 513, in the recording band, may be fixed and given by the ratio $(1+R_1/R_2)$ In preferred embodiments, the high-pass filtering stages are implemented with $g_m$–C filters since precision in the poles is not crucial. The closed-loop transfer function of the low-pass amplifier AMP1 may be set to have its dominant pole at 9 kHz (for 5 $\mu V_{peak}$ input neural signals), while providing the necessary further gain. Such DC gain is given by the ratio $(1+R_3/R_4)$. The DC restoration stage 517 may comprise a $g_{mo}$–$C_o$ high-pass filter, preferably with an input linear range higher than 0.2 V. Precision again is not crucial since this stage is only needed for compensation of the band-pass amplifying circuit offset. Finally, in FIG. 10B it can be observed that a reference voltage 522 is supplied as an input to the preamplifier 513 and the two low-pass amplifiers AMP1. In this embodiment, such reference voltage is provided by the sensing reference circuit 147 shown in FIGS. 3-5. This contributes to improving the PSRR of the band-pass amplifying circuit in the recording band, as explained below.

FIG. 10B shows a possible circuit for preamplifier 513. The M1 differential pairs realize the transconductance elements of a two-stage Differential Difference Amplifier (DDA). The current sources M3 are implemented using a cascode design as described in R. Gregorian and G. C. Temes, "Analog MOS Integrated Circuits for Signal Processing," pp. 131-133, John Wiley & Sons, 1986. This provides good matching of the two input stages, which is important in optimizing the performance of a DDA. On the other hand, the use of cascode current sources adds a PMOS threshold voltage $V_T$ to the minimum supply voltage $V_{DD}$ needed for operation; however, in this case the supply voltage $V_{DD}$, is typically not a limiting factor.

The differential current generated by transistors M1 is converted into a single-ended current by a cascode configuration, comprising transistors Q5 and cascode mirror M2. With this configuration, better frequency response can be achieved than in the case of an amplifier based on a cascade of two common-source stages. This is particularly true in the case of preamplifier 513, since the parasitic capacitance given by the large input transistors M1 (needed to achieve low-noise) is considerable. Transistor M10 provides further gain and accommodates the biasing of the output stage composed by M11, M12, Q13, and RD. The second stage of preamplifier 513 could comprise a single transistor but, in the preferred embodiment, comprises a transistor M10 with capacitors $C_{M1}$, and $R_M$ providing frequency compensation. See P. R. Gray and R. G. Meyer, "MOS Operational Amplifiers Design—a Tutorial Overview," *IEEE Journal of Solid-State Circuits*, sc-17(6):969-982, December 1982.

Finally, the equivalent Darlington pnp transistor M12-Q13 provides very low output impedance while drawing no current from the second stage. See A. R. Alvarez, *BiCMOS Technology and Applications*, pp. 317-318, 2d ed., Kluwer Academics Publishers, 1993. In this way, preamplifier 513 provides negligible systematic offset independent of variations in the electrical characteristics of the fabrication process. This is important for the successful performance of a DDA.

The transistors may be sized according to the methods presented by F. Silveira, D. Flandre and P. Jespers, "A gm/$I_D$ Based Methodology for the Design of CMOS Analog Circuits and Its Application to the Synthesis of a Silicon-On-Insulator Micropower OTA," *IEEE Journal of Solid-State Circuits*, 31(9):1314-1319, September 1996. These methods are based on the relation of the transconductance over drain current ratio ($g_m/I_D$), to the normalized current ($I_D/(W/L)$) and allow a unified treatment of all regions of operation of the MOSFET transistors. Sizing of the transistors can be achieved for example by using this method and the EKV model, with a set of parameters and measurements from the process. See E. A. Vittoz, *Micropower Techniques, Design of Analog Digital VLSI Circuits for Telecommunications and Signal Processing*, pp. 53 67, Eds. J. E. Franca and Y. P. Tsividis, Prentice Hall, 1993; and C. C. Enz et al., "An Analytical MOS Transistor Model Valid in All Regions of Operation and Dedicated to Low-Voltage and Low-Power Applications," *Analog Integrated Circuits and Signal Processing*, 8:83-114, 1995.

A main specification that applies to the preamplifier 513 is its noise level. The equivalent total input noise spectral density S1 has the following expression:

$$S_i = 4S_{M1} + S_{R2} + 4\left(\frac{g_{M2}}{g_{M1}}\right)^2 S_{M2} + 2\left(\frac{1}{g_{M1}R_a}\right)^2 S_{Ra} + \frac{S_{1/gm}}{A_{cDDA}^2 (f/f_{HPF})^2} \quad (1)$$

The factors in equation (1) are as follows:

$S_{M1}$ represents the noise contribution of an M1 input transistor. There are four of these transistors contributing directly to the input noise. The noise of preamplifier 513 is dominated by this factor.

$S_{R2}$ represents the noise contribution of resistance R2 that passes directly to the inputs 512.

$S_{M2}$ represents the noise contribution of a M2 current mirror transistor. The contribution of these loads is reduced by the square of the ratio of their transconductance to that of the input transistors M1.

$S_{Ra}$ represents the noise contribution of a $R_a$ resistor. The contribution of these resistors is also reduced by the square of the product of their value and the transconductance of the input transistors M1.

$S_{1/gm}$ is the noise of the equivalent resistor of the $g_m$–C high-pass filter. $S_{1/gm}$ is reduced by two factors. First of all, it is reduced by the gain of the preamplifier 513 ($A_{cDDA}$), since this stage precedes the filter, and second it decreases with frequency as stated in equation (1). This decrease is logical since, after the high-pass filter pole$_{FHPF}$ the capacitor C can be seen as a short circuit. This places the equivalent resistor $1/g_m$ in parallel with resistor R1.

A rough calculation shows that, in order to maintain a noise level from thermal sources which does not exceed approximately 0.6 $\mu V_{rms}$ in a 10 kHz bandwidth, the total equivalent input noise should be $\sqrt{S_i}$=6 nV/$\sqrt{Hz}$. Since in a well-designed amplifier the input transistors dominate the noise, the required level of MOSFET transconductance can be achieved only near weak inversion. The selection of the MOSFET type for the input transistors M1 was studied in detail. It is well known that in strong inversion the flicker noise of a PMOS transistor is lower than that of NMOS transistors. However, it has been reported that flicker noise in PMOS transistors may significantly increase when such transistors move from strong inversion toward weak inversion. See D. M. Binkley et al., "A Micropower CMOS, Direct-Conversion, VLF Receiver Chip, for Magnetic-Field Wireless Applications," *IEEE Journal of Solid-State Circuits*, 33(3):344-358, March 1998. Still others have reported the flicker noise going down, indicating that it arises from a mechanism that is strongly affected by details of device fabrication. The very severe increase in flicker noise has not been observed in prototype circuits according to this invention. Therefore, transistors M1 may be PMOS in some embodiments of the invention. In embodiments in which the band-pass amplifying circuit is fabricated using an N-well technology, this selection improves the PSRR of the circuit as well.

By implementing the transfer function of the band-pass amplifying circuit and the noise equation given by equation (1) in the MATLAB® design environment, thermal noise levels for each factor were assigned. This approach led to a value of $(g_m/I_D)$=16.81 V$^{-1}$ for the input transistors M1, that corresponds to a (W/L)=4480. Common-centroid crossed-coupling layouts may be used for transistors M1, R. P. Jindal, "Noise Associated with Distributed Resistance of MOSFET Gate Structures in Integrated Circuits," *IEEE Transactions on Electron Devices*, ed-31(10):1505-1509, October 1984, describes some common-centroid crossed-coupling layouts.

The load M2 in a prototype circuit according to the invention resulted deep in strong inversion because its transconductance was chosen almost five times lower than that of the input transistors to minimize noise. This resulted in a (W/L)=74.5. Resistors $R_a$ were dimensioned based on biasing requirements, noise minimization, and the folded cascode requirement that $g_{M5}R_a$>>1. This integrated resistor is made of a p$^+$ diffusion, with a typical value in the range of 64 to 96 to $\Omega/\square$ (ohms per square). In the currently preferred embodiment, $R_a$ has a value of 2245 $\Omega$.

The CMRR of the embodiment of preamplifier 13 shown in FIG. 10B may be expressed by:

$$CMRR = \frac{1}{\frac{1}{2g_{M1}R_{oM3}} \frac{\Delta g_{M1}}{g_{M1}} + \frac{\Delta \mu_1}{\mu_1}} \quad (2)$$

where $R_{oM3}$ is the output impedance of the cascode current source formed by transistors M3, $\Delta_{gM1}$ is the mismatch between the transconductances of transistors M1, $\mu_1$ is the voltage gain of transistors M1, and $\Delta\mu_1$ is the mismatch between the voltage gains of such transistors. Based on mismatch measurements previously performed for the present technology, the size of transistor M4 may be chosen to be (W/L)=20.3. Transistor M3 is composed of a few transistors M4 in order to provide the necessary bias current level for the input transistors M1. In this way, the CMRR given by equation (2) is mainly determined by the mismatch in the voltage gain $\mu_1$. CMRRs in the order of 95 dB can be achieved.

The output stage formed by M11, M12, Q13, and $R_D$, may be designed based on the excursion expected at output 514. Amplified EMG signals caused by mismatches in nerve cuffs as well as random offset of the preamplifier 513 should be taken into account.

The design of the second stage composed by M9, M10, $C_{M1}$, and $R_M$ was based on the minimization of systematic offset and the phase margin desired for the preamplifier 513.

In a prototype circuit according to the invention, transistors Q5-Q13 have an emitter area of 6.4×9.6 µm².

The connection of capacitor $C_{M1}$ between reference voltage 522 and the gate of one of the M2 transistors, as shown in FIG. 10B, improves the PSRR of preamplifier 513. As analyzed by E. Säckinger et al., "A General Relationship Between Amplifier Parameters, and Its Application to PSRR Improvement," *IEEE Transactions on Circuits and Systems* 38(10):1173-1181, October 1991, there is a constraint for the simultaneous improvement of the CMRR and the PSRR in any kind of amplifier. The PSRR of single-ended amplifiers can be improved and rejection in the mid-frequency range can be improved by connecting a capacitor between the amplifier input and a noise-free reference, in this case, reference voltage 522. This is the role capacitor $C_{M1}$ plays in the preamplifier 513.

Figure 10C:
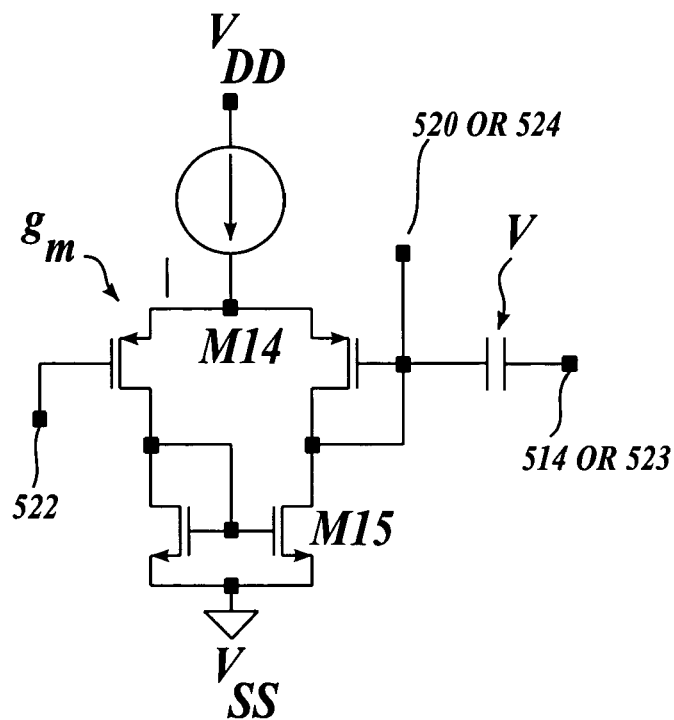

As mentioned above, band-pass amplifier 515 may be implemented by cascading two high-PSRR, first-order band-pass amplifiers, each composed of a $g_m$–C high-pass filter and a low-pass amplifying circuit. In FIG. 10C, the $g_m$–C high-pass filter is shown. The transconductance $g_m$ is provided by a basic differential pair with active load. All the transistors shown are placed in the moderate inversion region. This provides enough linear range for the present application.

Figure 10D:
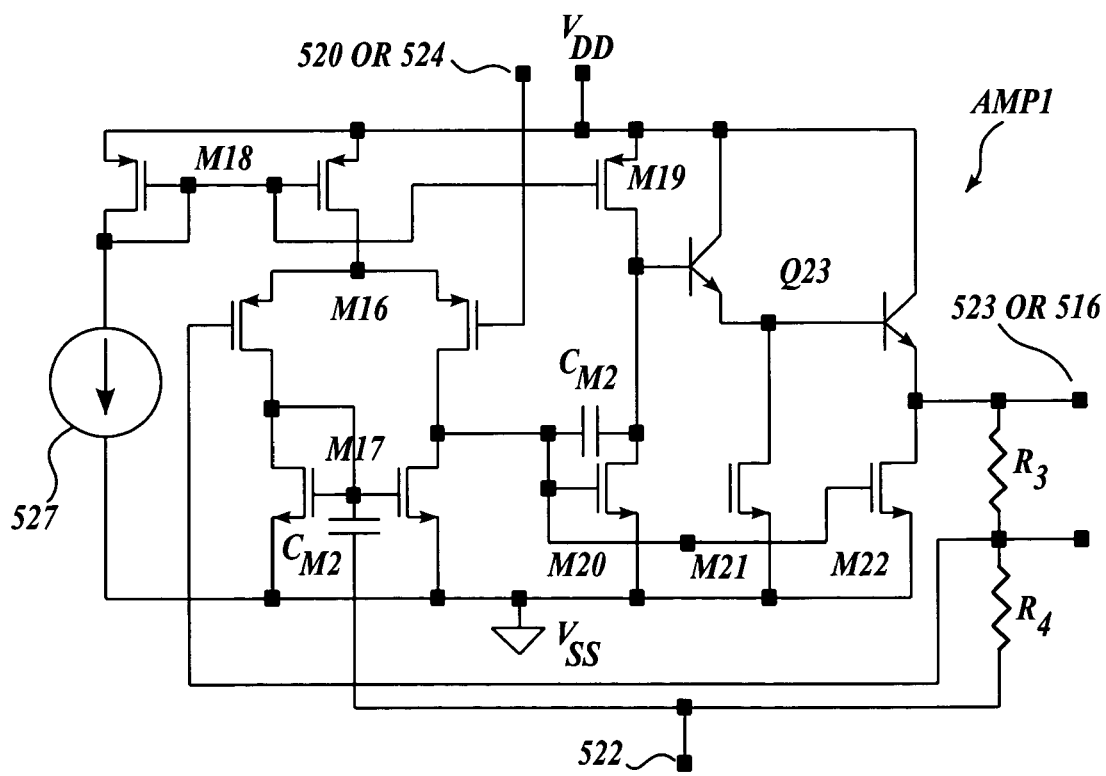

FIG. 10D shows a preferred embodiment of the amplifier AMP1. This is a Miller-type amplifier with a Darlington output stage that provides low-output impedance. Darlington transistors Q23 obtain their bias currents from transistors M21 and M22, which also carry signal current, making the amplifier a class AB. This reduces power consumption since it avoids the need of extra transistors to bias transistors Q23. Resistors $R_3$ and $R_4$ provide feedback for closed-loop operation. Since the two amplifiers AMP1 give the low-pass filter characteristic of the band-pass amplifying circuit, its cutoff frequency is set by the gain of this stage and by the high-pole specification of the band-pass amplifying circuit. Capacitor $C_{M2}$ connected between reference voltage 522 and the gates of transistors Ml7 increases the PSRR in the passed band, as explained above for the preamplifier 513.

Finally, in this invention, the DC restoration stage is implemented by an RC high-pass filter instead of the $g_{mo}$-$C_o$ high-pass filter mentioned before. The nominal cutoff frequency is preferably around 1300 Hz. This further helps to reduce noise of biological origin while allowing band-pass amplifying circuit to recover within a few milliseconds from overload such as could be caused by stimulation currents or while being cycled on/off. In the present invention, the cycling on/off of the amplifiers $A_i$ is preferably achieved by activating/deactivating the biasing currents 526, 527 in FIGS. 10B and 10D respectively.

In addition to the low-power, low-noise amplifiers $A_i$ described above, the signal conditioning circuits 180 also use precision rectifiers and bin integration circuits. FIGS. 11A-11G illustrate one embodiment of a rectifier circuit that follows the amplifier circuits $A_i$ in the signal conditioning path of the closed-loop nerve stimulation circuit described above. The rectifier is fully described in U.S. patent application Ser. No. 10/370,490, filed Feb. 24, 2003, which is herein incorporated by reference and is described below for completeness.

Figure 11A:
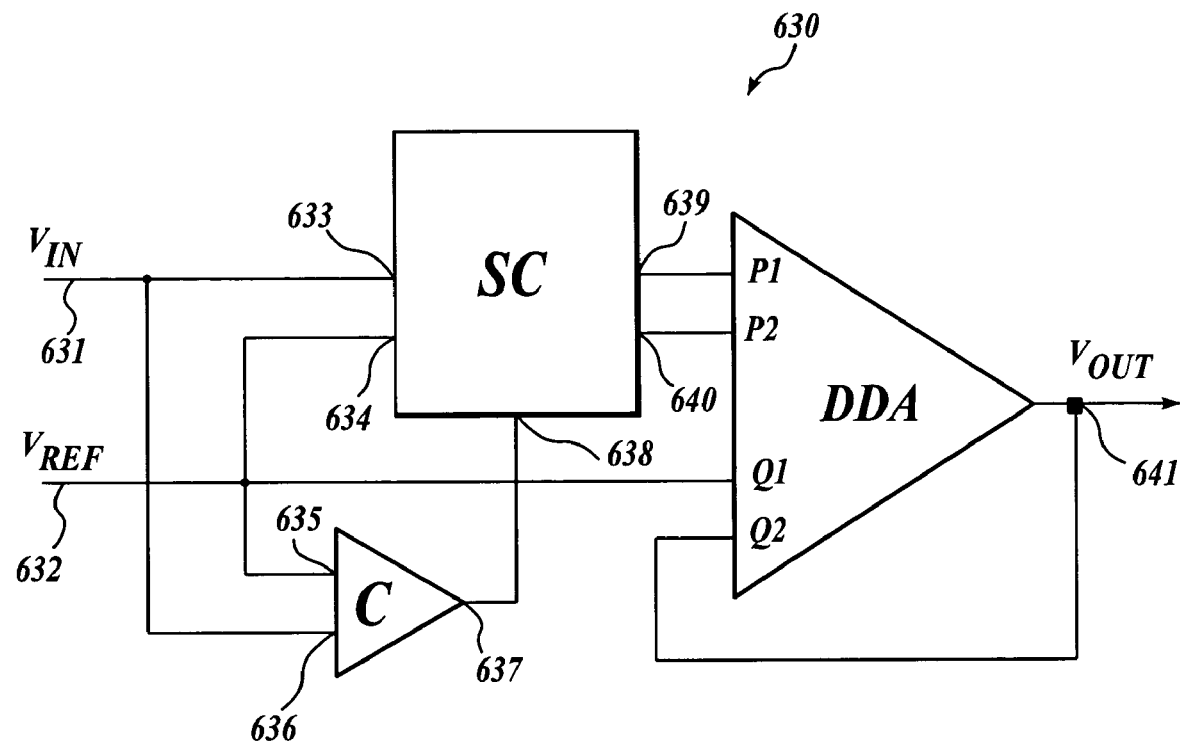
FIGS. 11A-11E illustrate one embodiment of a precision rectifier circuit for use with the closed-loop nerve signal sensing and electrical stimulation system of the present invention.

FIG. 11A is a schematic of a continuous-time rectifying circuit 630 for use with the closed-loop implantable nerve signal detection and stimulation systems of the present invention. In circuit 630, a first input 631 carrying a source signal ($V_{in}$) is connected to a first input 633 of a switching circuit (SC) and to a first input 636 of a polarity judgment circuit (C). A second input 632 carrying a reference signal ($V_{ref}$) is connected to a second input 634 of the switching circuit (SC) and to a second input 635 of the polarity judgment circuit (C).

In this invention, the reference signal ($V_{ref}$) is provided by sensing reference circuit 174. Output 637 of polarity judgment circuit (C) is connected to a control input 638 of switching circuit (SC). A first output 639 of switching circuit (SC) is connected to a first non-inverting input (P1) of a DDA. A second output 640 of switching circuit (SC) is connected to a first inverting input (P2) of the DDA. The second input 632 is also connected to a second non-inverting input (Q1) of the DDA. An output 641 of the DDA is connected to a second inverting input (Q2) of the DDA.

Figure 11B:
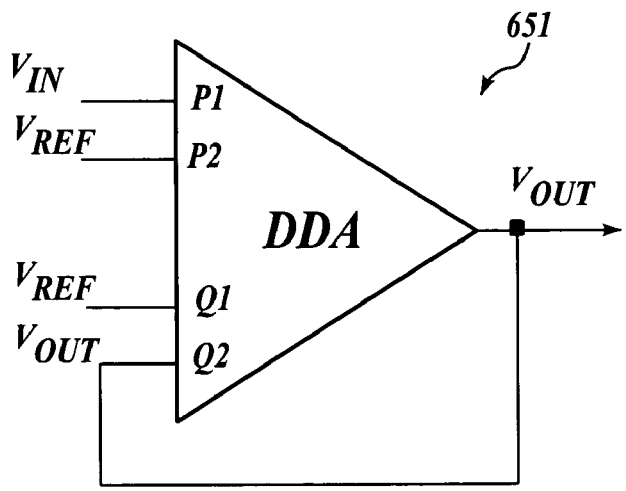
Figure 11C:
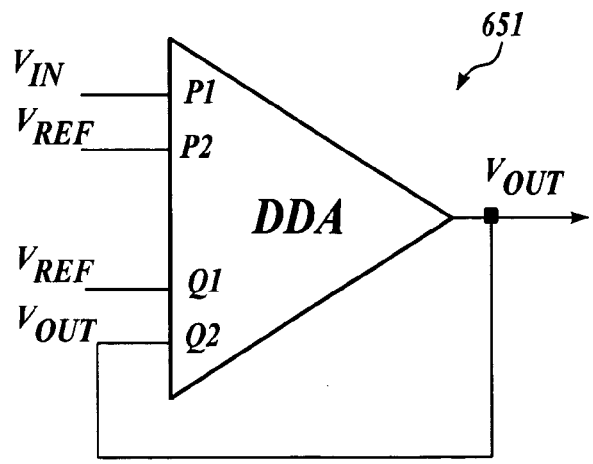

FIGS. 11B and 11C indicate the signals provided to each input terminal of the DDA during different phases of the operation of circuit 630. FIG. 11B shows a first connection pattern 650 in which switching circuit (SC) is in a first state and connects reference signal ($V_{ref}$) to the first non-inverting input (P1) of the DDA and source signal ($V_{in}$) to the first inverting input (P2) of the DDA. Together the first and second inputs (P1, P2) comprise a first differential pair of the DDA. FIG. 11B further shows the reference signal ($V_{ref}$) connected to a second non-inverting input (Q1), and the output signal ($V_{out}$) connected to a second inverting input (Q2) of the DDA. The second non-inverting input (Q1) and the second inverting input (Q2) together comprise a second differential pair of the DDA. FIG. 11C shows a second connection pattern 651 in which switching circuit (SC) is in a second state and connects source signal ($V_{in}$) to first input (P1) of the DDA and reference signal ($V_{ref}$) to second input (P2) of the DDA. The connections to the second differential pair (Q1, Q2) are the same in FIGS. 11B and 11C.

Switching circuit (SC) alternates between, its two states to provide DDA connection patterns 650 and 651 depending upon whether the source signal ($V_{in}$) is more positive than or less positive than the reference, signal ($V_{ref}$) as determined by polarity judgment circuit (C). For example, when the source signal ($V_{in}$) is at a potential which is more positive than the reference signal ($V_{ref}$), configuration pattern 650 is selected. When the source signal ($V_{in}$) is at a potential which is more negative than the reference signal ($V_{ref}$), configuration pattern 651 is selected. For positive half-wave rectification, when source signal ($V_{in}$) is more negative than reference signal ($V_{ref}$), a third configuration pattern may be selected in which reference signal ($V_{ref}$) is connected to both inputs (P1, P2) of the first differential pair, and the second differential pair remains as connected in FIGS. 11B and 11C.

Figure 11D:
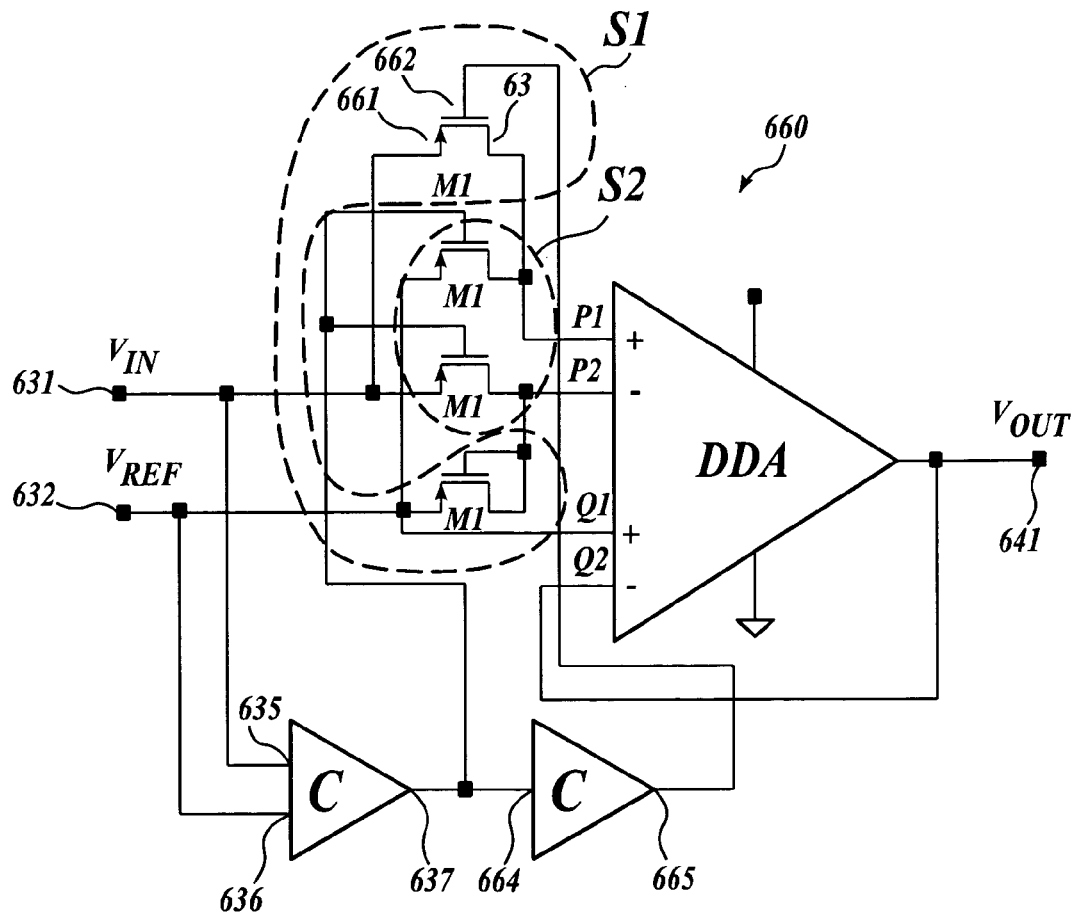

FIG. 11D shows a high-impedance, continuous-time full-wave rectifying circuit 660 according to a first preferred embodiment of the invention. In circuit 660, first input 631 carrying a source signal ($V_{in}$) is connected to a source 661 of a first switching element comprising a first FET (M1), to a source of a third switching element comprising a third FET (M3), and to an inverting input 635 of a polarity judgment circuit (C). Second input 632 carrying reference signal ($V_{ref}$) is connected to the sources of second and fourth switching elements comprising second and fourth FETs (M2, M4), to the non-inverting input 636 of the polarity judgment circuit (C), and to the non-inverting input (Q1) of the second differential pair of the DDA. The output signal ($V_{out}$) of the DDA is fed back to the inverting input (Q2) of this second differential pair.

A drain 663 of the first switching element (M1) and a drain of the second switching element (M2) are connected to the non-inverting input (P1) of the first differential pair of the DDA. A drain of the third switching element (M3) and a drain of the fourth switching element (M4) are connected to the inverting input (P2) of this first differential pair of the DDA.

The output 637 of the polarity judgment circuit (C) is connected to the input 664 of an inverter (T) and to a gate of the second switching element (M2) and a gate of the third switching element (M3). The complementary output 665 of the polarity judgment circuit (C) is provided by inverter (T) and is connected to a gate 662 of the first switching element (M1) and a gate of the fourth switching element (M4).

In FIG. 11D, the second (M2) and third (M3) switching elements together comprise a first switch set (S1), and the first (M1) and fourth (M4) switching elements together comprise a second switch set (S2). When the source signal ($V_{in}$) is more positive than the reference signal ($V_{ref}$), the output 637 of the polarity judgment circuit (C) has a low logical level. This causes the switches of the first switch set (S1) to be turned on and the switches of the second switch set (S2) to be turned off. Consequently, the reference signal ($V_{ref}$) is connected to the first non-inverting input (P1) of the DDA, and the source signal ($V_{in}$) is connected to the first inverting input (P2) of the DDA. When source signal ($V_{in}$) has a voltage less than the reference voltage then the switches of switch set (S1) are turned off and the switches of switch set (S2) are turned on so that the inputs of the DDA which ($V_{in}$) and ($V_{ref}$) are connected are reversed.

Figure 11E:
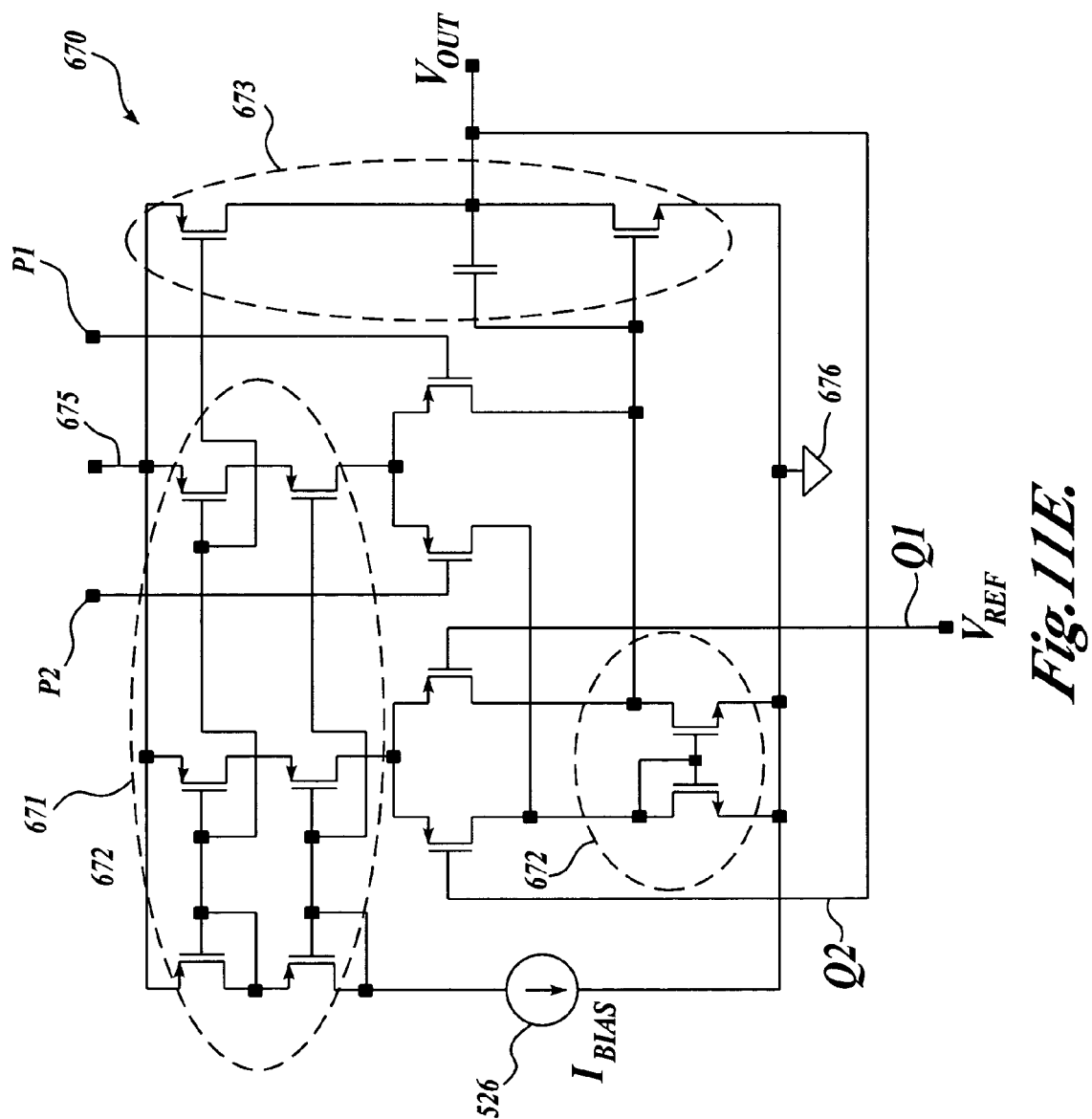

A DDA 670 which may be used to practice the invention is shown in FIG. 11E. A power supply (not shown) supplies power at point 675. A ground 676 provides a path for return current flow. The direction of the current bias ($I_{bias}$) is indicated. Current sources 671 for each differential pair are implemented using a circuit configuration which embodies the cascode technique; see R. Gregorian and G. C. Temes, "Analog MOS Integrated Circuits for Signal Processing," John Wiley & Sons, 1986, pp. 131-133. The cascode technique provides good matching of the first (P1, P2) and second (Q1, Q2) differential pairs. This is desirable to achieve high performance of the DDA. Current mirror 672 converts the differential current of the differential pairs to a single-ended current, which is provided to the output stage 673.

For positive full-wave rectification, the DDA produces an output signal with voltage as follows:

If $V_{in} > V_{ref}$ then $V_{out} = V_{in}$
If $V_{in} < V_{ref}$ then $V_{out} = -V_{in}$ For negative full-wave rectification, the DDA produces an output signal with voltage as follows:

If $V_{in} > V_{ref}$ then $V_{out} = -V_{in}$
If $V_{in} < V_{ref}$ then $V_{out} = V_{in}$ Since the situation where $V_{in} = V_{ref}$ is not important, a greater than equal condition ($\geq$) is equivalent to a greater than condition (>) and a less than equal condition ($\leq$) is equivalent to a less than condition (<). The DDA may optionally be configured to amplify its output signal by some gain factor.

As shown in the DDA equations above, when the source signal ($V_{in}$) is more positive than the reference signal ($V_{ref}$), the output signal ($V_{out}$) is equal to the source signal ($V_{in}$). When the source signal ($V_{in}$) is more negative than the reference signal ($V_{ref}$), the symmetric condition to the one described above happens, resulting in output signal ($V_{out}$) being equal to the negative value of the source signal ($-V_{in}$). Therefore, the output signal ($V_{out}$) is the positive rectified version of the source signal ($V_{in}$). Alternatively, if a negative rectified output is desired, the connections to the inputs 635, 636 of the polarity judgment circuit (C) can be reversed such that the source signal ($V_{in}$) is connected to the non-inverting input 636 and the reference signal ($V_{ref}$) is connected to the inverting input 635 of polarity judgment circuit (C). This alternate configuration yields the second set of DDA equations above for the negative full-wave rectification.

Preferred embodiments of the invention require only a small die area because it is not necessary to use any resistors or floating diodes. Consequently, the invention can be fully integrated on a chip in CMOS technology. A low threshold voltage allows circuits according to the invention to be used to rectify low level bioelectrical signals such as signals picked up by nerve cuff electrodes. The full integration of a rectifying circuit having a low threshold voltage enables embodiments of the invention to be especially suitable for use in implantable biomedical devices. For example, a chip which bears a rectifier circuit according to the invention may be incorporated in an implantable device for rectifying nerve signals collected by electrodes for use in a system for manipulating a prosthetic device. A further benefit of requiring only a small die area is that several rectifier circuits of the invention can be integrated into the same implantable device together with other circuits. For example, one or more rectifying circuits according to the invention may be combined with one or more signal conditioning circuits such as amplifiers, filters, or the like on a single integrated circuit chip, which may be a CMOS chip.

As will be apparent to those skilled in the art in the light of the foregoing disclosure, many alterations and modifications are possible in the practice of the invention without departing from the spirit or scope thereof. For example:

the first and second switch sets (S1, S2) are each shown in the embodiment of FIG. 11D as comprising two switching elements, however the first and second switch sets (S1, S2) can be configured in a variety of ways, including as a plurality of switching elements, and any of FETs M1, M2, M3 or M4 may be replaced with other suitable electronic switches which, in their "ON" states offer sufficiently low thresholds.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

The embodiments of the invention in which an exclusive property or privilege is claimed are defined as follows:

1. A fully implantable nerve stimulation system, comprising:
 at least one nerve cuff so configured as to receiving part of a nerve, the nerve cuff having electrodes therein positioned in the vicinity of nerve fibers;
 a control unit including:
  a power source;
  a processor;
  at least one signal conditioning circuit so connected to the electrodes of the at least one nerve cuff as to receive signals from the nerve fibers;
  at least one stimulation circuit so connected to the electrodes of the at least one nerve cuff as to deliver stimulation pulses to the nerve fibers;
  wherein the processor is so configured as to a) selectively activate the at least one signal conditioning circuit in order to detect at least one gait phase transition event and b) activate the at least one stimulation circuit in response to the detection of the at least one gait phase transition event.

2. The implantable nerve stimulation system of claim 1, wherein the at least one signal conditioning circuit includes:
 a low input current amplifier;
 a rectifier circuit; and
 an integrator circuit.

3. The implantable nerve stimulation system of claim 2, wherein the nerve stimulation system stimulates nerve fibers to treat foot drop and wherein the gait phase transition event includes the occurrence of a heel contact or toe lift event.

4. The implantable nerve stimulation system of claim 3, wherein the processor is so configured as to activate the at least one stimulation circuit in response to the detection of a toe lift event.

5. The implantable nerve stimulation system of claim 3, wherein the processor disables the at least one signal conditioning circuits during at least a portion of the time when the at least one stimulation circuit is activated.

6. The implantable nerve stimulation system of claim 3, wherein the processor is so configured as to detect the occurrence of a heel contact or toe lift event by filtering output signals produced by the at least one signal conditioning circuit and comparing the filtered output signals with the unfiltered output signals to detect a rising or falling ramp in the output signals and wherein the processor activates the at least one stimulation circuit so as to cause at least one stimulation pulse to be delivered to the nerve fibers upon detection of a toe lift event.

7. The implantable nerve stimulation system of claim 6, wherein the control unit further includes a thigh orientation determination circuit in communication with the processor, the thigh orientation determination circuit producing a signal indicative of the angle of a patient's thigh, and wherein the processor is so configured as to adjust the stimulation pulses delivered by the at least one stimulation circuit in response to the angle of the patient's thigh.

8. The implantable nerve stimulation system of claim 7, wherein the processor is so configured as to terminate the activation of the at least one stimulation circuit upon detection of a heel contact event if the signal indicative of the patient's thigh angle indicates the patient is walking on a relatively flat surface.

9. The implantable nerve stimulation system of claim 7, wherein the processor is so configured as to enable the at least one signal conditioning circuit periodically when the signal indicative of the patient's thigh angle indicates the patient's thigh is horizontal.

10. The implantable nerve stimulation system of claim 7, wherein the processor is so configured as to enable the at least one signal conditioning circuit more frequently when the signal indicative of the patient's thigh angle indicates the patient's thigh is vertical.

11. The implantable nerve stimulation system of claim 7, wherein the thigh orientation determination circuit includes an accelerometer circuit.

12. The implantable nerve stimulation system of claim 11, wherein the thigh accelerometer circuit includes a pair of orthogonally oriented accelerometers.

13. The implantable nerve stimulation system of claim 7, wherein the processor is so configured as to terminate the activation of the at least one stimulation circuit upon detection of a second toe lift event if the signal indicative of the patient's thigh angle indicates the patient is walking on a stair.

14. The implantable nerve stimulation system of claim 7, wherein the processor is so configured as to increase the magnitude of the stimulation pulses delivered by the stimulation circuit if the signal indicative of the patient's thigh angle indicates the patient is walking up a stair.

15. The implantable nerve stimulation system of claim 7, wherein the processor is so configured as to decrease the magnitude of the stimulation pulses delivered by the stimulation circuit if the signal indicative of the patient's thigh angle indicates that the patient is walking down a stair.

16. The implantable nerve stimulation system of claim 7, wherein the processor is so configured as to reduce the power drawn from the power source if the signal indicative of the angle of the patient's thigh indicates the patient is not standing.

17. The implantable nerve stimulation system of claim 6, wherein the at least one nerve cuff includes a first nerve cuff so configured as to receive part of the tibial nerve and a second nerve cuff so configured as to receive part of the common peroneal nerve.

18. The implantable nerve stimulation system of claim 6, wherein the at least one nerve cuff includes a nerve cuff so configured as to receive part of the common peroneal nerve.

19. The implantable nerve stimulation system of claim 6, wherein the at least one nerve cuff includes a nerve cuff so configured as to receive part of the sciatic nerve.

20. The implantable nerve stimulation system of claim 3, wherein the control unit further comprises:
    a thigh orientation determination circuit so configured as to produce signals indicative of the angle of a patient's thigh and wherein the processor is so configured as to adjust the power drawn from the electrical power source in response to the thigh angle.

21. The implantable nerve stimulation system of claim 20, wherein the processor adjusts the stimulation pulse delivered to the electrodes in response to the thigh angle.

22. The implantable nerve stimulation system of claim 20, wherein the processor is so configured as to operate in a plurality of modes that are dependent in part on the signal indicative of the angle of the patient's thigh.

23. The implantable nerve stimulation system of claim 22, wherein the processor is so configured as to reduce power drawn from the power source when the signal indicative of the angle of the patient's thigh indicates that the patient's thigh is substantially horizontal.

24. The implantable nerve stimulation system of claim 22, wherein the processor is so configured as to detect heel contact or toe lift events from output signals produced by the at least one signal conditioning circuit when the signal indicative of the angle of the patient's thigh indicates that the patient is standing.

25. The implantable nerve stimulation system of claim 24, wherein the processor is so configured as to detect heel contact or toe lift events from filtered and unfiltered output signals produced by the at least one signal conditioning circuit.

26. The implantable nerve stimulation system of claim 25, wherein the filtered output signals are filtered with a morphological filter.

27. The implantable nerve stimulation system of claim 22, wherein the processor is so configured as to adjust the delivered stimulation pulses as a function of the signal indicative of the angle of the patient's thigh.

28. The implantable nerve stimulation system of claim 22, wherein the processor is so configured as to disable the at least one signal conditioning circuit when a stimulation pulse is being delivered to the electrodes of one of the at least one nerve cuff.

29. The implantable nerve stimulation system of claim 22, wherein the processor is so configured as to periodically enable the at least one signal conditioning circuit wherein the signal indicative of the angle of the patient's thigh indicates that the patient's thigh is substantially horizontal.

30. The implantable nerve stimulation system of claim 20, wherein the thigh orientation determination circuit includes an accelerometer circuit.

31. The implantable nerve stimulation system of claim 30, wherein the thigh accelerometer circuit includes a pair of orthogonally oriented accelerometers.

32. The implantable nerve stimulation system of claim 3, wherein the control unit further comprises:
a programmable switch so controlled by the processor as to selectively couple one of the at least one signal conditioning circuit to the electrodes of one of the at least one signal conditioning circuit.

33. The implantable nerve stimulation system of claim 1, wherein the control unit further includes a thigh orientation determination circuit in communication with the processor, the a thigh orientation determination circuit producing a signal indicative of an orientation of a patient's thigh, and wherein the processor disables components of the control unit when the signal indicative of the orientation of the patient's thigh indicates that the patient's thigh is substantially horizontal.

34. The implantable nerve stimulation system of claim 33, wherein the processor is so configured as to adjust the delivered stimulation pulses as a function of the orientation of the patient's thigh.

35. The implantable nerve stimulation system of claim 33, wherein the thigh orientation determination circuit includes an accelerometer circuit.

36. The implantable nerve stimulation system of claim 35, wherein the thigh accelerometer circuit includes a pair of orthogonally oriented accelerometers.

37. The implantable nerve stimulation system of claim 1, wherein the power source includes a battery.

38. The implantable nerve stimulation system of claim 37, wherein the battery is rechargeable.

39. The implantable nerve stimulation system of claim 1, wherein the control unit further includes a communication circuit that communicates with an external programmer to adjust the operation of the processor.

40. The implantable nerve stimulation system of claim 39, wherein the external programmer can adjust which electrodes the at least one signal conditioning circuit is connected to, and which electrodes receive the stimulation pulses.

41. The implantable nerve stimulation system of claim 1, wherein the nerve stimulation system is so configured as to stimulate a patient's muscle, and wherein the processor is so configured as to operate in a user initiated exercise mode such that the at least one stimulation circuit is activated for a selectable period of time to exercise the patient's muscle.

42. The implantable nerve stimulation system of claim 1, wherein the processor selectively enables the at least one conditioning circuit and the at least one stimulation circuit so as to lengthen the life of the power source.

43. The implantable nerve stimulation system of claim 1, wherein the processor is further so configured as to process the at least one gait phase transition event in order to determine a patient's gait phase and activate the at least one stimulation circuit in response to the patient's gait phase.

44. A fully implantable nerve stimulation system, comprising:
at least one nerve cuff so configured as to receiving part of a nerve, the nerve cuff having electrodes therein positioned in the vicinity of nerve fibers;
a control unit including:
a power source;
a processor;
at least one signal conditioning circuit so connected to the electrodes of the at least one nerve cuff as to receive signals from the nerve fibers;
at least one stimulation circuit so connected to the electrodes of the at least one nerve cuff as to deliver stimulation pulses to the nerve fibers;
wherein the processor is so configured as to a) selectively activate the at least one signal conditioning circuit, b) analyse the signals received by the at least one signal conditioning circuit so as to detect either a positive ramp having a duration between a first and a second values and a peak-to-baseline difference greater than a first threshold value or a negative ramp having a duration between a third and a fourth values and a peak-to-baseline difference greater than a second threshold value and c) activate the at least one stimulation circuit in response to the detection of either the positive ramp having a duration between the first and the second values and a peak-to-baseline difference greater than the first threshold value or the negative ramp having a duration between the third and the fourth values and a peak-to-baseline difference greater than the second threshold value.

45. The implantable nerve stimulation system of claim 44, wherein the first value is 50 ms and the second value is 150 ms.

46. The implantable nerve stimulation system of claim 44, wherein the third value is 150 ms and the fourth value is 300 ms.

47. A fully implantable nerve stimulation system, comprising:
at least one nerve cuff so configured as to receiving pad of a nerve, the nerve cuff having electrodes therein positioned in the vicinity of nerve fibers;
a control unit including:
a power source;
a processor;
a thigh orientation determination circuit producing a signal indicative of an orientation of a patient's thigh;
at least one signal conditioning circuit so connected to the electrodes of the at least one nerve cuff as to receive signals from the nerve fibers;
at least one stimulation circuit so connected to the electrodes of the at least one nerve cuff as to deliver stimulation pulses to the nerve fibers;
wherein the processor is so configured as to a) selectively activate the at least one signal conditioning circuit in order to detect a physiological event b) activate the at least one stimulation circuit in response to the detection of the physiological event and c) adjust an output of the at least one stimulation circuit in response to the orientation of the patient's thigh.

48. The implantable nerve stimulation system of claim 47, wherein to at least one signal conditioning circuit includes:
a low input current amplifier;
a rectifier circuit; and
an integrator circuit.

49. The implantable nerve stimulation system of claim 48, wherein the nerve stimulation system stimulates nerve fibers to treat foot drop and wherein the physiological event is the occurrence of a heel contact or toe lift event.

50. The implantable nerve stimulation system of claim 49, wherein the processor is so configured as to activate the at least one stimulation circuit in response to the detection of a toe lift event.

51. The implantable nerve stimulation system of claim 50, wherein the processor disables the at least one signal conditioning circuits during at least a portion of the time when the at least one stimulation circuit is activated.

52. The implantable nerve stimulation system of claim 49, wherein the processor is so configured as to detect the occurrence of a heel contact or toe lift event by filtering output signals produced by the at least one signal conditioning circuit and comparing the filtered output signals with the unfiltered output signals to detect a rising or falling ramp in the output signals and wherein the processor activates the at least one stimulation circuit so as to cause at least one stimulation pulse to be delivered to the nerve fibers upon detection of a toe lift event.

53. The implantable nerve stimulation system of claim 49, wherein the processor is so configured as to terminate the activation of the at least one stimulation circuit upon detection of a heel contact event if the signal indicative of the patient's thigh orientation indicates the patient is walking on a relatively flat surface.

54. The implantable nerve stimulation system of claim 49, wherein the processor is so configured as to terminate the activation of the at least one stimulation circuit upon detection of a second toe lift event if the signal indicative of the patient's thigh orientation indicates the patient is walking on a stair.

55. The implantable nerve stimulation system of claim 49, wherein the processor is so configured as to increase the magnitude of the stimulation pulses delivered by the stimulation circuit if the signal indicative of the patient's thigh orientation indicates the patient is walking up a stair.

56. The implantable nerve stimulation system of claim 49, wherein the processor is so configured as to decrease the magnitude of the stimulation pulses delivered by the stimulation circuit if the signal indicative of the patient's thigh orientation indicates that the patient is walking down a stair.

57. The implantable nerve stimulation system of claim 49, wherein the processor is so configured as to reduce the power drawn from the power source if the signal indicative of the orientation of the patient's thigh indicates the patient is not standing.

58. The implantable nerve stimulation system of claim 49, wherein the at least one nerve cuff includes a first nerve cuff so configured as to receive part of the tibial nerve and a second nerve cuff so configured as to receive part of the common peroneal nerve.

59. The implantable nerve stimulation system of claim 49, wherein the at least one nerve cuff includes a nerve cuff so configured as to receive part of the common peroneal nerve.

60. the implantable nerve stimulation system of claim 49, wherein the at least one nerve cuff includes a nerve cuff so configured as to receive part of the sciatic nerve.

61. The implantable nerve stimulation system of claim 49, wherein the processor is so configured as to adjust the power drawn from the electrical power source in response to the thigh orientation.

62. The implantable nerve stimulation system of claim 49, wherein the control unit further comprises:
 a programmable switch so controlled by the processor as to selectively couple one of the at least one signal conditioning circuit to the electrodes of one of the at least one signal conditioning circuit.

63. The implantable nerve stimulation system of claim 49, wherein the processor is so configured as to enable the at least one signal conditioning circuit periodically when the signal indicative of the patient's thigh orientation indicates the patient's thigh is horizontal.

64. The implantable nerve stimulation system of claim 49, wherein the processor is so configured as to enable the at least one signal conditioning circuit more frequently when the signal indicative of the patient's thigh orientation indicates the patient's thigh is vertical.

65. The implantable nerve stimulation system of claim 49, wherein the processor is so configured as to operate in a plurality of modes that are dependent in part on the signal indicative of the orientation of the patient's thigh.

66. The implantable nerve stimulation system of claim 65, wherein the processor is so configured as to reduce power drawn from the power source when the signal indicative of the orientation of the patient's thigh indicates that the patient's thigh is substantially horizontal.

67. The implantable nerve stimulation system of claim 65, wherein the processor is so configured as to detect heel contact or toe lift events from output signals produced by the at least one signal conditioning circuit when the signal indicative of the orientation of the patient's thigh indicates that the patient is standing.

68. The implantable nerve stimulation system of claim 67, wherein the processor is so configured as to detect heel contact or toe lift events from filtered and unfiltered output signals produced by the at least one signal conditioning circuit.

69. The implantable nerve stimulation system of claim 68, wherein the filtered output signals are filtered with a morphological filter.

70. The implantable nerve stimulation system of claim 65, wherein the processor is so configured as to disable the at least one signal conditioning circuit when a stimulation pulse is being delivered to the electrodes of one of the at least one nerve cuff.

71. The implantable nerve stimulation system of claim 65, wherein the processor is so configured as to periodically enable the at least one signal conditioning circuit wherein the signal indicative of the orientation of the patient's thigh indicates that the patient's thigh is substantially horizontal.

72. The implantable nerve stimulation system of claim 47, wherein the processor disables components of the control unit when the signal indicative of the orientation of the patient's thigh indicates that the patient's thigh is substantially horizontal.

73. The implantable nerve stimulation system of claim 72, wherein the processor is so configured as to adjust the delivered stimulation pulses as a function of the orientation of the patient's thigh.

74. The implantable nerve stimulation system of claim 47, wherein the thigh orientation determination circuit includes an accelerometer.

75. The implantable nerve stimulation system of claim 74, wherein the thigh accelerometer circuit includes a pair of orthogonally oriented accelerometers.

76. The implantable nerve stimulation system of claim 47, wherein the power source includes a battery.

77. The implantable nerve stimulation system of claim 76, wherein the battery is rechargeable.

78. The implantable nerve stimulation system of claim 47, wherein the control unit further includes a communication circuit that communicates with an external programmer to adjust the operation of the processor.

79. The implantable nerve stimulation system of claim 78, wherein the external programmer can adjust which electrodes the at least one signal conditioning circuit is connected to, and which electrodes receive the stimulation pulses.

80. The implantable nerve stimulation system of claim 47, wherein the nerve stimulation system is so configured as to stimulate a patient's muscle, and wherein the processor is so configured as to operate in a user initiated exercise mode such that the at least one stimulation circuit is activated for a selectable period of time to exercise the patient's muscle.

81. The implantable nerve stimulation system of claim 47, wherein the processor selectively enables the at least one conditioning circuit and the at least one stimulation circuit so as to lengthen the life of the power source.

* * * * *